United States Patent [19]
Litchholt et al.

[11] Patent Number: 5,895,379
[45] Date of Patent: Apr. 20, 1999

[54] ABSORBENT CORES HAVING IMPROVED ACQUISITION CAPABILITY, AND ABSORBENT ARTICLES CONTAINING THEM

[75] Inventors: John Joseph Litchholt, Harrison; Glen Ray Lash; Amy Gray Hughes, both of Cincinnati, all of Ohio

[73] Assignee: The Procter & Gamble Company, Cincinnati, Ohio

[21] Appl. No.: 08/957,407

[22] Filed: Oct. 23, 1997

Related U.S. Application Data

[63] Continuation of application No. 08/620,622, Mar. 22, 1996, abandoned.
[51] Int. Cl.$^6$ ..................................................... A61F 13/15
[52] U.S. Cl. ........................ 604/378; 604/385.1; 604/368
[58] Field of Search ................................. 604/358, 368, 604/370, 372, 328, 324, 325, 385.1

[56] References Cited

U.S. PATENT DOCUMENTS

| | | | |
|---|---|---|---|
| 4,560,372 | 12/1985 | Pieniak | 604/368 |
| 4,781,711 | 11/1988 | Houghton et al. | 604/378 |
| 4,790,839 | 12/1988 | Ahr. | |
| 4,973,325 | 11/1990 | Sherrod et al. | |
| 4,988,344 | 1/1991 | Reising et al. | |
| 4,988,345 | 1/1991 | Reising. | |

(List continued on next page.)

FOREIGN PATENT DOCUMENTS

| | | |
|---|---|---|
| 0 388 372 A1 | 9/1990 | European Pat. Off. |
| 0 640 330 A1 | 3/1995 | European Pat. Off. |
| 0 695 541 A1 | 2/1996 | European Pat. Off. |
| 695541 | 2/1996 | European Pat. Off. |
| 0 700 672 | 3/1996 | European Pat. Off. |
| 0 700 673 A1 | 3/1996 | European Pat. Off. |
| 700673 | 3/1996 | European Pat. Off. |

(List continued on next page.)

OTHER PUBLICATIONS

Le Khac et al; Fibersord™ Superaborsbent Fibers & Web Development, 5–87; INDA Assc. of the Non–Woven Industry pp. 513–524.

Primary Examiner—Robert A. Clarke
Attorney, Agent, or Firm—Carl J. Roof; Kevin D. Hogg; Jacobus C. Rasser

[57] ABSTRACT

The invention relates to an absorbent core capable of absorbing discharged aqueous body fluids, said absorbent core comprising:

(1) an upper fluid acquisition/distribution component capable of receiving aqueous fluids, the fluid acquisition/distribution components being positioned in the fluid discharge region of the absorbent core;

(2) at least one upper fluid storage component positioned at least partially underneath and in fluid communication with the upper fluid acquisition/distribution component(s), the upper fluid storage component being capable of expanding in the z-direction when contacted with aqueous body fluids to form a fluid acquisition zone;

(3) a fluid acquisition zone capable of receiving aqueous body fluids, the fluid acquistion zone being at least partially surrounded by said a least one upper fluid storage component(s);

(4) a lower fluid acquisition/distribution component capable of acquiring and transporting aqueous body fluids being positioned at least partially underneath and in fluid communication with the upper fluid storage component(s); and (5) preferably, at least one lower fluid storage component positioned underneath the lower fluid acquisition/distribution component and in fluid communication therewith.

The invention further relates to an absorbent article useful for absorbing discharged aqueous body fluids that comprises: A) a fluid pervious topsheet; B) a backsheet; and C) an absorbent core of the present invention.

38 Claims, 4 Drawing Sheets

U.S. PATENT DOCUMENTS

| | | | |
|---|---|---|---|
| 5,087,506 | 2/1992 | Palumbo . | |
| 5,147,345 | 9/1992 | Young et al. | 604/378 |
| 5,294,478 | 3/1994 | Wanek et al. . | |
| 5,300,053 | 4/1994 | Genaro . | |
| 5,300,054 | 4/1994 | Feist et al. | 604/378 |
| 5,304,161 | 4/1994 | Noel et al. . | |
| 5,331,015 | 7/1994 | DesMarais et al. | 604/369 |
| 5,387,207 | 2/1995 | Dyer et al. | 604/369 |
| 5,411,497 | 5/1995 | Tanzer et al. | 604/378 |
| 5,425,725 | 6/1995 | Tanzer et al. | 604/378 |
| 5,433,715 | 7/1995 | Tanzer et al. | 604/378 |
| 5,454,800 | 10/1995 | Hirt et al. | 604/378 |
| 5,466,513 | 11/1995 | Wanek et al. . | |
| 5,486,167 | 1/1996 | Dragoo et al. | 604/358 |
| 5,509,915 | 4/1996 | Hanson et al. . | |
| 5,531,728 | 7/1996 | Lash | 604/374 |
| 5,562,646 | 10/1996 | Goldman et al. | 604/368 |

FOREIGN PATENT DOCUMENTS

| | | | |
|---|---|---|---|
| | 705587 | 4/1996 | European Pat. Off. . |
| | 2636899 | 3/1977 | Germany . |
| | 2208477 | 4/1989 | United Kingdom . |
| | 2286832 | 8/1995 | United Kingdom . |
| | 2296438 | 7/1996 | United Kingdom . |
| | 92/11831 | 7/1992 | WIPO . |
| WO | 94/02092 | 2/1994 | WIPO . |
| WO | 94/07546 | 4/1994 | WIPO . |
| WO | 95/10995 | 4/1995 | WIPO . |
| | 95/11652 | 5/1995 | WIPO . |
| | 95/11653 | 5/1995 | WIPO . |
| | 95/11654 | 5/1995 | WIPO . |
| WO | 95/11651 | 5/1995 | WIPO . |
| | 95/21596 | 8/1995 | WIPO . |
| WO | 95/21596 | 8/1995 | WIPO . |
| | 96/03947 | 2/1996 | WIPO . |

ABSORBENT CORES HAVING IMPROVED ACQUISITION CAPABILITY, AND ABSORBENT ARTICLES CONTAINING THEM

This is a continuation of application Ser. No. 08/620,622, filed on Mar. 22, 1996, abandoned.

TECHNICAL FIELD

This application relates to absorbent articles such as diapers, adult incontinence pads, sanitary napkins, and the like capable of handling multiple discharges of aqueous body fluids. The application particularly relates to articles comprising an absorbent core having a fluid acquistion zone, formed by the swelling of a fluid storage material, positioned beneath a fluid acquisition/distribution material.

BACKGROUND OF THE INVENTION

The development of highly absorbent members for use as disposable diapers, adult incontinence pads and briefs, and catamenial products such as sanitary napkins, are the subject of substantial commercial interest. A highly desired characteristic for such products is thinness. For example, thinner diapers are less bulky to wear, fit better under clothing, and are less noticeable. They are also more compact in the package, making the diapers easier for the consumer to carry and store. Compactness in packaging also results in reduced distribution costs for the manufacturer and distributor, including less shelf space required in the store per diaper unit.

The ability to provide thinner absorbent articles such as diapers has been contingent on the ability to develop relatively thin absorbent cores or structures that can acquire and store large quantities of discharged body fluids, in particular urine. In this regard, the use of certain absorbent polymers often referred to as "hydrogels," "superabsorbents" or "hydrocolloid" material has been particularly important. See, for example, U.S. Pat. No. 3,669,103 (Harper et al), issued Jun. 13, 1972, and U.S. Pat. No. 3,670,731 (Harmon), issued Jun. 20, 1972, that disclose the use of such absorbent polymers (hereafter "hydrogel-forming absorbent polymers") in absorbent articles. Indeed, the development of thinner diapers has been the direct consequence of thinner absorbent cores that take advantage of the ability of these hydrogel-forming absorbent polymers to absorb large quantities of discharged aqueous body fluids, typically when used in combination with a fibrous matrix. See, for example, U.S. Pat. No. 4,673,402 (Weisman et al), issued Jun. 16, 1987 and U.S. Pat. No. 4,935,022 (Lash et al), issued Jun. 19, 1990, that disclose dual-layer core structures comprising a fibrous matrix and hydrogel-forming absorbent polymers useful in fashioning thin, compact, nonbulky diapers.

Prior to the use of these hydrogel-forming absorbent polymers, it was general practice to form absorbent structures, such as those suitable for use in infant diapers, entirely from wood pulp fluff. Given the relatively low amount of fluid absorbed by wood pulp fluff on a gram of fluid absorbed per gram of wood pulp fluff, it was necessary to employ relatively large quantities of wood pulp fluff, thus necessitating the use of relatively bulky, thick absorbent structures. The introduction of these hydrogel-forming absorbent polymers into such structures has allowed the use of less wood pulp fluff. These hydrogel-forming absorbent polymers are superior to fluff in their ability to absorb large volumes of aqueous body fluids, such as urine (i.e., at least about 15 g/g), thus making smaller, thinner absorbent structures feasible.

Prior absorbent structures have generally comprised relatively low amounts (e.g., less than about 50% by weight) of these hydrogel-forming absorbent polymers. See, for example, U.S. Pat. No. 4,834,735 (Alemany et al), issued May 30, 1989 (preferably from about 9 to about 50% hydrogel-forming absorbent polymer in the fibrous matrix). There are several reasons for this. The hydrogel-forming absorbent polymers employed in prior absorbent structures have generally not had an absorption rate that would allow them to quickly absorb body fluids, especially in "gush" situations. This has necessitated the inclusion of fibers, typically wood pulp fibers, to serve as temporary reservoirs to hold the discharged fluids until absorbed by the hydrogel-forming absorbent polymer.

More importantly, many of the known hydrogel-forming absorbent polymers exhibited gel blocking. "Gel blocking" occurs when particles of the hydrogel-forming absorbent polymer are wetted and the particles swell so as to inhibit fluid transmission to other regions of the absorbent structure. Wetting of these other regions of the absorbent member therefore takes place via a very slow diffusion process. In practical terms, this means acquisition of fluids by the absorbent structure is much slower than the rate at which fluids are discharged, especially in gush situations. Leakage from the absorbent article can take place well before the particles of hydrogel-forming absorbent polymer in the absorbent member are fully saturated or before the fluid can diffuse or wick past the "blocking" particles into the rest of the absorbent member. Gel blocking can be a particularly acute problem if the particles of hydrogel-forming absorbent polymer do not have adequate gel strength and deform or spread under stress once the particles swell with absorbed fluid. See U.S. Pat. No. 4,834,735 (Alemany et al), issued May 30, 1989.

This gel blocking phenomena has typically necessitated the use of a fibrous matrix in which are dispersed the particles of hydrogel-forming absorbent polymer. This fibrous matrix keeps the particles of hydrogel-forming absorbent polymer separated from one another. This fibrous matrix also provides a capillary structure that allows fluid to reach the hydrogel-forming absorbent polymer located in regions remote from the initial fluid discharge point. See U.S. Pat. No. 4,834,735 (Alemany et al), issued May 30, 1989. However, dispersing the hydrogel-forming absorbent polymer in a fibrous matrix at relatively low concentrations in order to minimize or avoid gel blocking can lower the overall fluid storage capacity of thinner absorbent structures. Also, absorbent cores comprising hydrogel-forming absorbent polymers dispersed uniformly throughout the fibrous matrix will typically not have the ability to rapidly acquire and distribute fluids during "gush" situations or when the core has become saturated from prior discharges of body fluids.

The need for rapidly acquiring and distributing discharge body fluids has led to the development of dual-layer core structures noted above. These dual-layer core structures basically comprise: (1) an upper fibrous layer adjacent to the fluid pervious topsheet that is substantially free of hydrogel-forming absorbent polymers that acquires the discharged fluid; and (2) a lower layer that stores this acquired fluid and is typically either: (a) a fibrous matrix having hydrogel-forming absorbent polymers uniformly dispersed therein; or (b) a laminate structure where hydrogel-forming absorbent polymer is between two tissue layers. See, for example, U.S. Pat. No. 4,673,402 (Weisman et al), issued Jun. 16, 1987. See also U.S. Pat. No. 4,935,022 (Lash et al), issued Jun. 19, 1990 and U.S. Pat. No. 5,217,445 (Young et al), issued Jun.

8, 1993, where certain chemically stiffened curly, twisted cellulosic fibers are used in this upper layer to provide improved acquisition and distribution performance. Another variation is to "profile" the absorbent core such that there is an acquisition zone substantially free of hydrogel-forming absorbent polymers in the fluid discharge area and a storage area having dispersed therein hydrogel-forming absorbent polymers that is in fluid communication with the acquisition zone. See U.S. Pat. No. 4,834,735 (Alemany et at), issued May 30, 1989 and U.S. Pat. No. 5,047,023 (Berg), issued Sep. 10, 1991.

Even with the fluid handling improvements provided by these prior absorbent designs, it has been found that the ability to readily acquire fluid diminishes rapidly as the absorbent core becomes saturated with aqueous body fluids. This occurs because the void spaces between fibers and the hydrogel-forming absorbent polymers in the absorbent core become partially filled with fluid during the first "gush" and therefore can not rapidly accept the necessary volume of fluid during subsequent "gushes". Furthermore, the risk of leakage increases as the number of loads increases.

Another problem that can occur with some prior absorbent core designs is a phenomenon referred to as "rewet." Rewet occurs when there is acquired fluid that is freely mobile and available in that portion of the absorbent core adjacent the topsheet. This is typically experienced as the absorbent core becomes saturated with acquired fluid. Under mechanical pressure from the wearer of the article, this mobile fluid is pumped out of the absorbent core and upwards through the topsheet. As a result, the topsheet becomes "rewetted" with this pumped fluid such that there is not adequate topsheet dryness.

Accordingly, it would also be desirable to provide an absorbent core that: (1) has an absorbent material, capable of swelling upon absorbing discharged body fluid to form a fluid acquisition zone, in the absorbent core for desired total fluid capacity and thinness; (2) is able to acquire discharged fluid rapidly during "gush" situations, even when the core has become saturated in the loading area from prior discharges of fluids; and (3) when incorporated into an absorbent article, preferably minimizes rewetting of the topsheet.

SUMMARY OF THE INVENTION

The present invention relates to an absorbent core capable of absorbing discharged aqueous body fluids, the absorbent core comprising:

(1) an upper fluid acquisition/distribution component capable of receiving aqueous fluids, the fluid acquisition/distribution components being positioned in the fluid discharge region of the absorbent core;

(2) at least one upper fluid storage component positioned at least partially underneath and in fluid communication with the upper fluid acquisition/distribution component, said at least one fluid storage component being capable of expanding in the z-direction when contacted with aqueous body fluids to form a fluid acquisition zone;

(3) a fluid acquisition zone capable of receiving aqueous body fluids, the fluid acqustion zone being at least partially surrounded by said at least one upper fluid storage component and positioned at least partially beneath the fluid discharge region of the absorbent core;

(4) a lower fluid acquisition/distribution component capable of acquiring and transporting aqueous body fluids, the lower fluid acquisition/distribution component being positioned at least partially underneath and in fluid communication with said at least one upper fluid storage component; and (5) preferably, at least one lower fluid storage component positioned underneath the lower fluid acquisition/ distribution component and in fluid communication therewith, at least a portion of this lower storage component being positioned underneath the fluid acquisition zone.

The present invention further relates to an absorbent article useful for absorbing discharged aqueous body fluids that comprises: A) a fluid pervious topsheet; B) a backsheet; and C) an absorbent core of the present invention.

The absorbent articles of the present invention have an improved ability to rapidly acquire, distribute and store discharged body fluids due to the presence of: (1) the fluid acquisition zone that is formed by the swellable fluid storage component(s); and (2) the upper fluid acquisition/ distribution component that is capable of receiving gushes of body fluids and rapidly desorbing these gushes to other components of the core. The positioning of the fluid storage component(s), which is essential in forming the fluid acquisitions zone, to beneath the upper fluid acquistion/ distribution component offers the benefit of providing a large area for acquiring fluid—i.e. fluid can be initially acquired even if it enters the diaper outside the fluid acquisition zone; and the acquisition/distribution material provides an aesthetically soft feel next to the wearer's skin, compared with certain of the material used as the upper fluid storage component (e.g., hydrogel-forming polymer). This is important during "gush" situations or when portions of the absorbent core become saturated from prior multiple discharges of such fluids. The absorbent articles of the present invention also minimize rewetting of the topsheet, in-part due to the locating of the fluid acquistion zone remote from the wearer's skin. This provides good skin dryness for the wearer of an article containing the cores of the present invention.

DETAILED DESCRIPTION OF THE INVENTION

A. Definitions

Figure 1:
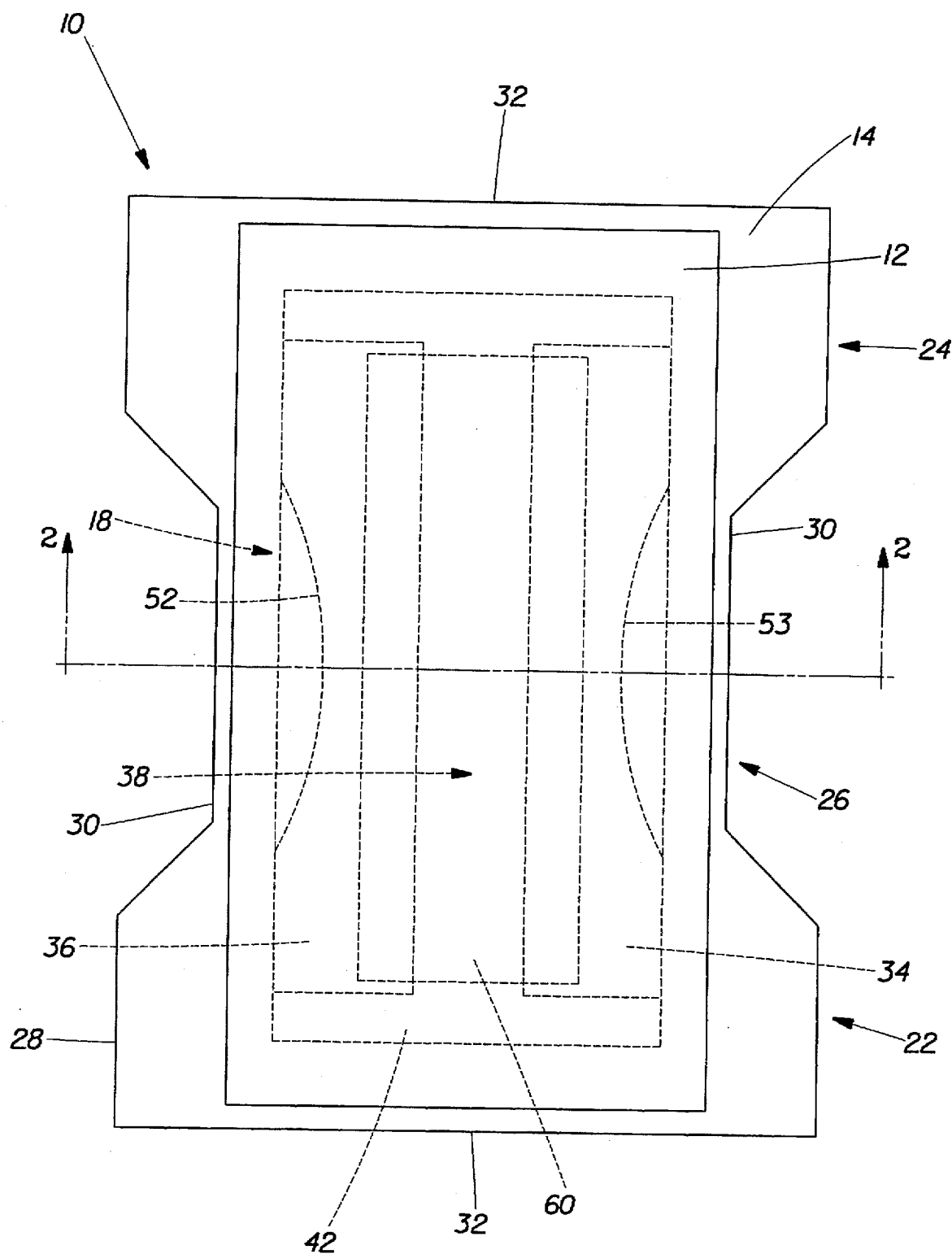
FIG. 1 is a top plan view of an absorbent article according to the present invention where the topsheet is transparent so as to more clearly show the absorbent core.

As used herein, the term "aqueous body fluids" includes urine, menses and vaginal discharges.

As used herein, "direct communiciation" means that fluid can transfer readily between two absorbent article components (e.g., the upper storage component(s) and the lower fluid acquisition/distribution component) without substantial accumulation, transport, or restriction by an interposed layer. For example, tissues, nonwoven webs, construction adhesives, and the like may be present between the upper acquisition/distribution layer and upper storage layer while maintaining "direct communication" as long as they do not substantially accumulate (store), transport (wick), or restrict the fluid as it passes from the storage layer to the acquisition/distribution layer.

As used herein, the term "Z-dimension" refers to the dimension orthogonal to the length and width of the member, core or article. The Z-dimension usually corresponds to the thickness of the member, core or article.

As used herein, the term "X-Y dimension" refers to the plane orthogonal to the thickness of the member, core or article. The X and Y dimensions correspond to the length and width, respectively, of the member, core or article.

As used herein, the term "absorbent core" refers to the component of the absorbent article that is primarily responsible for fluid handling properties of the article, including acquiring, transporting, distributing and storing aqueous body fluids. As such, the absorbent core typically does not include the topsheet or backsheet of the absorbent article.

As used herein, the term "load" or "gush" generally refers to an insult or depostion of urine or other bodily fluid that would typically result during use. The term load may also refer to the total amount of liquid contained in an absorbent article, but typically refers to one fluid insult.

As use herein, the term "layer" refers to an absorbent member whose primary dimension is X-Y, i.e., along its length and width. It should be understood that the term layer is not necessarily limited to single layers or sheets of material. Thus the layer can comprise laminates or combinations of several sheets or webs of the requisite type of materials. Accordingly, the term "layer" includes the terms "layers" and "layered."

For purposes of this invention, it should also be understood that the term "upper" refers to absorbent core components, such as layers, that are nearest to the wearer of the absorbent article, and are typically nearer the topsheet of an absorbent article; conversely, the term "lower" refers to absorbent core components that are furthermost away from the wearer of the absorbent article and are typically nearer the backsheet.

As used herein, the term "comprising" means various components, steps and the like can be conjointly employed according to the present invention. Accordingly, the term "comprising" encompasses the more restrictive terms "consisting essentially of" and "consisting of," these latter, more restrictive terms having their standard meaning as understood in the art.

All percentages, ratios and proportions used herein are by weight unless otherwise specified.

B. Absorbent Core Components

Exemplary core components useful in achieving improved acquisition performance are described below.

1. Upper and Lower Fluid Acquisition/Distribution Components

The cores of the present invention comprise an upper and a lower fluid acquisition/distribution component. The respective fluid acquisition/distribution components can provide a variety functions in the absorbent cores of the present invention. One function, particularly for the upper acquisition/distribution component, is to initially acquire the discharged body fluids. Another key function is to transport and distribute these acquired fluids to other absorbent core components, and in particular the fluid storage components of the absorbent core. In some instances, the fluid acquisition/distribution components according to the present invention can include at least some hydrogel-forming absorbent polymer and thus provide some fluid storage capacity for the absorbent core.

The detailed description that follows refers generally to the materials useful as either/both of the acquistion/distribution components. Though referred to in the singular, the description applies to both of these core components. As incorporated into the cores, the upper and lower components may be substantially the same, or they may be different, as discussed below.

The fluid acquisition/distribution component of the present invention can comprise a variety of fibrous materials that form fibrous webs or fibrous matrices. Fibers useful in the fluid acquisition/distribution component include those that are naturally occurring fibers (modified or unmodified), as well as synthetically made fibers. Examples of suitable unmodified/modified naturally occurring fibers include cotton, Esparto grass; bagasse, kemp, flax, silk, wool, wood pulp, chemically modified wood pulp, jute, rayon, ethyl cellulose, and cellulose acetate. Suitable synthetic fibers can be made from polyvinyl chloride, polyvinyl fluoride, polytetrafluoroethylene, polyvinylidene chloride, polyacrylics such as ORLON®, polyvinyl acetate, polyethylvinyl acetate, non-soluble or soluble polyvinyl alcohol, polyolefins such as polyethylene (e.g., PULPEX®) and polypropylene, polyamides such as nylon, polyesters such as DACRON® or KODEL®, polyurethanes, polystyrenes, and the like. The fibers used can comprise solely naturally occurring fibers, solely synthetic fibers, or any compatible combination of naturally occurring and synthetic fibers.

The fibers useful in fluid acquisition/distribution components of the present invention can be hydrophilic, hydrophobic fibers that are made hydrophilic, or can be a combination of both hydrophilic and hydrophilized hydrophobic fibers. As used herein, the term "hydrophilic" describes fibers, or surfaces of fibers, that are wettable by aqueous fluids (e.g., aqueous body fluids) deposited on these fibers. Hydrophilicity and wettability are typically defined in terms of contact angle and the surface tension of the fluids and solids involved. This is discussed in detail in the American Chemical Society publication entitled *Contact Angle, Wettability and Adhesion*, edited by Robert F. Gould (Copyright 1964). A fiber, or surface of a fiber, is said to be wetted by a fluid (i.e., hydrophilic) when either the contact angle between the fluid and the fiber, or its surface, is less than 90°, or when the fluid tends to spread spontaneously across the surface of the fiber, both conditions to normally co-existing. Conversely, a fiber or surface is considered to be hydrophobic if the contact angle is greater than 90° and the fluid does not spread spontaneously across the surface of the fiber.

Other fibers useful as the fluid aquistition/distribution component are hydrophobic fibers that are wettable due to their geometry. Such fibers include "capillary channel fibers" such as those described in U.S. Pat. No. 5,200,248, to Thompson et al. and U.S. Pat. No. 5,268,229, to Phillips et al, both of which are incorporated by reference herein.

Suitable hydrophilic fibers for use in the present invention include cellulosic fibers, modified cellulosic fibers, rayon, polyester fibers such as polyethylene terephthalate (e.g., DACRON®), hydrophilic nylon (HYDROFIL®), and the like. Suitable hydrophilic fibers can also be obtained by hydrophilizing hydrophobic fibers, such as surfactant-treated or silica-treated thermoplastic fibers derived from, for example, polyolefins such as polyethylene or polypropylene, polyacrylics, polyamides, polystyrenes, polyurethanes and the like. For reasons of availability and cost, cellulosic fibers, in particular wood pulp fibers, are preferred for use in the present invention.

Suitable wood pulp fibers can be obtained from well-known chemical processes such as the Kraft and sulfite processes. It is especially preferred to derive these wood pulp fibers from southern soft woods due to their premium absorbency characteristics. These wood pulp fibers can also be obtained from mechanical processes, such as ground wood, refiner mechanical, thermomechanical, chemimechanical, and chemi-thermomechanical pulp processes. Recycled or secondary wood pulp fibers, as well as bleached and unbleached wood pulp fibers, can be used.

A desirable source of hydrophilic fibers for use in the present invention are chemically stiffened cellulosic fibers. As used herein, the term "chemically stiffened cellulosic fibers" means cellulosic fibers that have been stiffened by chemical means to increase the stiffness of the fibers under both dry and aqueous conditions. Such means can include the addition of a chemical stiffening agent that, for example, coats and/or impregnates the fibers. Such means can also include the stiffening of the fibers by altering the chemical structure, e.g., by crosslinking polymer chains.

Polymeric stiffening agents that can coat or impregnate the cellulosic fibers include: cationic modified starches having nitrogen-containing groups (e.g., amino groups) such as those available from National Starch and Chemical Corp., Bridgewater, N.J., USA; latexes; wet strength resins such as polyamide-epichlorohydrin resin (e.g., Kymene® 557H, Hercules, Inc. Wilmington, Del., USA), polyacrylamide resins described, for example, in U.S. Pat. No. 3,556,932 (Coscia et al), issued Jan. 19, 1971; commercially available polyacrylamides marketed by American Cyanamid Co., Stamford, Conn., USA, under the tradename Parez® 631 NC; urea formaldehyde and melamine formaldehyde resins, and polyethylenimine resins. A general dissertation on wet strength resins utilized in the paper art, and generally applicable herein, can be found in TAPPI monograph series No. 29, "Wet Strength in Paper and Paperboard", Technical Association of the Pulp and Paper Industry (New York, 1965).

These fibers can also be stiffened by chemical reaction. For example, crosslinking agents can be applied to the fibers that, subsequent to application, are caused to chemically form intrafiber crosslink bonds. These crosslink bonds can increase the stiffness of the fibers. While the utilization of intrafiber crosslink bonds to chemically stiffen the fiber is preferred, it is not meant to exclude other types of reactions for chemical stiffening of the fibers. Fibers stiffened by crosslink bonds in individualized form (i.e., the individualized stiffened fibers, as well as processes for their preparation) are disclosed, for example, in U.S. Pat. No. 3,224,926 (Bernardin), issued Dec. 21, 1965; U.S. Pat. No. 3,440,135 (Chung), issued Apr. 22, 1969; U.S. Pat. No. 3,932,209 (Chatterjee), issued Jan. 13, 1976; and U.S. Pat. No. 4,035,147 (Sangenis et al), issued Jul. 12, 1977. More preferred stiffened fibers are disclosed in U.S. Pat. No. 4,822,453 (Dean et al), issued Apr. 18, 1989; U.S. Pat. No. 4,888,093 (Dean et al), issued Dec. 19, 1989; U.S. Pat. No. 4,898,642 (Moore et al), issued Feb. 6, 1990; and U.S. Pat. No. 5,137,537 (Herron et al), issued Aug. 11, 1992, all of which are incorporated by reference. In the more preferred stiffened fibers, chemical processing includes intrafiber crosslinking with crosslinking agents while such fibers are in a relatively dehydrated, defibrated (i.e., individualized), twisted, curled condition. See, for example, U.S. Pat. No. 4,898,642.

These chemically stiffened cellulosic fibers have certain properties that can make them particularly useful in fluid acquisition/distribution components according to the present invention, relative to unstiffened cellulosic fibers. In addition to being hydrophilic, these stiffened fibers have unique combinations of stiffness and resiliency. This allows thermally bonded fluid acquisition/distribution components made with these fibers to maintain high levels of absorptivity, and to exhibit high levels of resiliency and an expansionary responsiveness to wetting. In particular, the resiliency of these stiffened fibers enables the fluid acquisition/distribution component to better maintain its capillary structure in the presence of both fluid and compressive forces normally encountered during use and are thus more resistant to collapse.

In the case of thermally bonded fluid acquisition/distribution components useful in the present invention, a thermoplastic material is included with the fibers. Upon melting, at least a portion of this thermoplastic material migrates to the intersections of the fibers, typically due to interfiber capillary gradients. These intersections become bond sites for the thermoplastic material. When cooled, the thermoplastic materials at these intersections solidify to form the bond sites that hold the matrix or web of fibers together in each of the respective layers.

Amongst its various effects, bonding at these fiber intersections increases the overall compressive modulus and strength of the resulting thermally bonded fluid acquisition/distribution component. In the case of the chemically stiffened cellulosic fibers, the melting and migration of the thermoplastic material also has the effect of increasing the average pore size of the resultant web, while maintaining the density and basis weight of the web as originally formed. This can improve the fluid acquisition properties of the thermally bonded fluid distribution component upon initial discharges, due to improved fluid permeability, and upon subsequent discharges, due to the combined ability of the stiffened fibers to retain their stiffness upon wetting and the ability of the thermoplastic material to remain bonded at the fiber intersections upon wetting and upon wet compression. In net, thermally bonded webs of stiffened fibers retain their original overall volume, but with the volumetric regions previously occupied by the thermoplastic material becoming open to thus increase the average interfiber capillary pore size.

Thermoplastic materials useful in fluid distribution components of the present invention can be in any of a variety of forms including particulates, fibers, or combinations of particulates and fibers. Thermoplastic fibers are a particularly preferred form because of their ability to form numerous interfiber bond sites. Suitable thermoplastic materials can be made from any thermoplastic polymer that can be melted at temperatures that will not extensively damage the fibers that comprise the primary web or matrix of each layer.

Preferably, the melting point of this thermoplastic material will be less than about 190° C., and preferably between about 75° C. and about 175° C. In any event, the melting point of this thermoplastic material should be no lower than the temperature at which the thermally bonded absorbent structures, when used in absorbent articles, are likely to be stored. The melting point of the thermoplastic material is typically no lower than about 50° C.

The thermoplastic materials, and in particular the thermoplastic fibers, can be made from a variety of thermoplastic polymers, including polyolefins such as polyethylene (e.g., PULPEX®) and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the foregoing such as vinyl chloride/ vinyl acetate, and the like. One preferred thermoplastic binder fiber is PLEXAFIL® polyethylene microfibers (made by DuPont) that are also available as an about 20% blend with 80% cellulosic fibers sold under the tradename KIT-TYHAWK® (made by Weyerhaeuser Co.). Depending upon the desired characteristics for the resulting thermally bonded absorbent member, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, polyurethanes and the like. The surface of the hydrophobic thermoplastic fiber can be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij® 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants can also be used. These surfactants can be applied to the thermoplastic fibers at levels of, for example, from about 0.2 to about 1 g. per sq. of centimeter of thermoplastic fiber.

Suitable thermoplastic fibers can be made from a single polymer (monocomponent fibers), or can be made from more than one polymer (e.g., bicomponent fibers). As used herein, "bicomponent fibers" refers to thermoplastic fibers that comprise a core fiber made from one polymer that is encased within a thermoplastic sheath made from a different polymer. The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers can include sheath/core fibers having the following polymer combinations: polyethylene/polypropylene, polyethylvinyl acetate/ polypropylene, polyethylene/polyester, polypropylene/ polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND® or CHISSO® bicomponent fibers). These bicomponent fibers can be concentric or eccentric. As used herein, the terms "concentric" and "eccentric" refer to whether the sheath has a thickness that is even, or uneven, through the cross-sectional area of the bicomponent fiber. Eccentric bicomponent fibers can be desirable in providing more compressive strength at lower fiber thicknesses. Suitable bicomponent fibers for use herein can be either uncrimped (i.e. unbent) or crimped (i.e. bent). Bicomponent fibers can be crimped by typical textile means such as, for example, a stuffer box method or the gear crimp method to achieve a predominantly two-dimensional or "flat" crimp.

In the case of thermoplastic fibers, their length can vary depending upon the particular melt point and other properties desired for these fibers. Typically, these thermoplastic fibers have a length from about 0.3 to about 7.5 cm long, preferably from about 0.4 to about 3.0 cm long, and most preferably from about 0.6 to about 1.2 cm long. The properties, including melt point, of these thermoplastic fibers can also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers can have a decitex in the range from about 1.0 to about 20, preferably from about 1.4 to about 10, and most preferably from about 1.7 to about 3.3.

The compressive modulus of these thermoplastic materials, and especially that of the thermoplastic fibers, can also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers can be used to alter the properties, and especially the density characteristics, of the respective absorbent members during preparation of the absorbent core.

As noted previously, in some absorbent cores according to the present invention, the fluid acquisition/distribution component can include hydrogel-forming absorbent to provide some fluid storage capacity for the core. In those instances, the fluid acquisition/distribution component can comprise up to about 50% hydrogel-forming absorbent polymer. Preferably, the fluid distribution component comprises up to about 30% hydrogel-forming absorbent polymer. Most preferably, the fluid distribution component comprises up to about 15% hydrogel-forming absorbent polymer. For the upper fluid/acquisition/distribution component, it is generally preferred that there be essentially no hydrogel-forming polymer.

The fluid acquisition/distribution component can also or alternatively comprise a polymeric foam material. Particularly suitable absorbent foams have been made from HIPEs. Though they differ with respect to certain properties from those foams discussed as being useful as the fluid storage component, the foams are open-celled, polymeric materials. See, for example, U.S. Pat. No. 5,260,345 (DesMarais et al), issued Nov. 9, 1993 and U.S. Pat. No. 5,268,224 (DesMarais et al), issued Dec. 7, 1993. These absorbent HIPE foams provide desirable fluid handling properties, including: (a) relatively good wicking and fluid distribution characteristics to transport the imbibed urine or other body fluid into the unused portion of the absorbent article to allow for subsequent gushes of fluid to be accommodated; and (b) a relatively high storage capacity with a relatively high fluid capacity under load, i.e. under compressive forces. These HIPE absorbent foams are also sufficiently flexible and soft so as to provide a high degree of comfort to the wearer of the absorbent article. See also U.S. Pat. No. 5,147,345 (Young et al), issued Sep. 15, 1992 and U.S. Pat. No. 5,318,554 (Young et al), issued Jun. 7, 1994, which discloses absorbent cores having a fluid acquisition/distribution component that can be a hydrophilic, flexible, open-celled foam such as a melamine-formaldehyde foam (e.g., BASOTECT made by BASF), and a fluid storage/redistribution component that is a HIPE-based absorbent foam.

These foam-based acquisition/distribution components should allow rapid fluid acquisition, as well as efficient partitioning or distribution of fluid to other components of the absorbent core having higher absorption pressures than the desorption pressure of the acquisition/distribution foam. This property of fluid desorption to other core components is important in enhancing the ability to accept repeated discharges or loadings of fluid and to maintain the skin dryness of the wearer. It also allows the acquisition/distribution foam to serve as a void volume reservoir, or buffer zone, to temporarily hold fluid that can be expressed from the storage components of the core when extraordinarily high pressures are encountered during use of the absorbent article.

In giving this fluid to other core components, these foam-based acquisition/distribution components should do so without densifying or collapsing. Foam-based acquisition/distribution components should also readily accept fluid, with or without the aid of gravity. Foam-based acquisition/distribution components should further provide good aesthetics, be soft and resilient in structure, and have good physical integrity in both wet and dry states.

Other foams useful as such acquisition/distribution components are described and claimed in co-pending U.S. Ser. No. 08/370,695, filed Jan. 10, 1995, by Stone, et al., which is incorporated by reference herein. These foams offer improved fluid retention and desorption (i.e., ability to relinquish fluid to other absorption components) properties, resulting from the processing conditions described therein. Briefly, the ability to provide these improved foams lies with the use of low shear conditions and a robust emulsifier system during HIPE processing.

Still other foams useful as the acquisition/distribution componenets are described and claimed in co-pending U.S. Ser. No. 08/520,793, filed Aug. 30, 1995 by DesMarais, which is incorporated herein by reference. These foams offer still better acquisition and desorption properties, again because of advancements made in the processing (e.g., low shear) and the emulsifier employed.

2. Fluid Storage Component(s)

The materials useful as the fluid storage component include materials that are capable of absorbing large quantities of aqueous body fluids, with or without other optional components such as fibers, thermoplastic material, etc. In addition to these properties, to materials used as the upper fluid storage component must be capable of swelling in the z-direction upon imbibing fluid, so as to form the fluid acquisition zone. Materials capable of performing as the upper fluid storage component(s) include substantially water-insoluble, water swellable absorbent polymer materials commonly referred to as "hydrogels", "hydrocolloids", or "superabsorbent" materials (for the purposes of the present invention, these materials are collectively referred to as "hydrogel-forming absorbent polymers"); and open-celled foam materials that remain in a collapsed (i.e., unexpanded) state until contacted with aqueous body fluids.

A principle function of these fluid storage components is to absorb the discharged body fluids either directly or from other absorbent core components (e.g., the fluid acquisition/distribution component), and then retain such fluids, even when subjected to pressures normally encountered as a result of the wearer's movements. Another important function of the upper storage component(s) is their ability to swell to form the fluid acquisition zone. (It should be understood that the fluid storage component(s) can serve functions other than fluid storage and formation of a fluid acquisition zone, such as improving body fit.)

Regardless of the material used, it is preferred that the upper storage component be capable of expanding in the z-direction from the dry, compressed state by at least 100% when fully saturated. Such z-directional expansion will effectively increase the volume of the fluid acquisition zone. However, those skilled in the art will recognize that the width and length of the fluid acquisition zone is also important to overall volume, and materials that do not swell in the z-direction by 100% may still be useful herein.

a. Hydrogel-forming Absorbent Polymers

When hydrogel polymers are used, an important aspect of these fluid storage components according to the present invention is that they contain a relatively high concentration of the absorbent polymers. In order to provide relatively thin absorbent articles capable of absorbing and retaining large quantities of body fluids, it is desirable to increase the level of these hydrogel-forming absorbent polymers and to reduce the level of other components, in particular fibrous components. In measuring the concentration of hydrogel-forming absorbent polymer, the percent by weight of the hydrogel-forming polymer relative to the combined weight of hydrogel-forming polymer and any other components (e.g., fibers, thermoplastic material, etc.) that are present in the fluid storage component is used. With this in mind, the concentration of the hydrogel-forming absorbent polymers in a given fluid storage component according to the present invention can be in the range of from about 50 to 100%, preferably from about 60 to 100%, more preferably from about 70 to 100%, and most preferably from about 80 to 100%, by weight of the storage component(s).

A wide variety of hydrogel-forming absorbent polymers can be used in the fluid storage components of the present invention. These hydrogel-forming absorbent polymers have a multiplicity of anionic, functional groups, such as sulfonic acid, and more typically carboxy, groups. Examples of absorbent polymers suitable for use herein include those which are prepared from polymerizable, unsaturated, acid-containing monomers, including the olefinically unsaturated acids and anhydrides that contain at least one carbon to carbon olefinic double bond. More specifically, these monomers can be selected from olefinically unsaturated carboxylic acids and acid anhydrides, olefinically unsaturated sulfonic acids, and mixtures thereof. See U.S. Pat. No. 5,324,561 (Rezai et al), issued Jun. 23, 1994 (herein incorporated by reference), which describes suitable absorbent polymers and their preparation.

Preferred hydrogel-forming absorbent polymers for use in the present invention contain carboxy groups. These include hydrolyzed starch-acrylonitrile graft copolymers, partially neutralized starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478.

Most preferred hydrogel-forming absorbent polymers for use in the present invention are slightly network crosslinked polymers of partially neutralized polyacrylic acids and starch derivatives thereof. Most preferably, the absorbent polymers comprise from about 50 to about 95%, preferably about 75%, neutralized, slightly network crosslinked, polyacrylic acid (i.e. poly (sodium acrylate/acrylic acid)). Processes for network crosslinking the polymers and typical network crosslinking agents are described in greater detail in the hereinbefore-referenced U.S. Pat. No. 4,076,663.

The hydrogel-forming absorbent polymers can be formed in any conventional manner. Preferred methods for forming these absorbent polymers are those that involve aqueous solution or other solution polymerization methods. See, for example, U.S. Reissue Pat. No. 32,649 (Brandt et al), reissued Apr. 19, 1988. While it is preferred that the absorbent polymers be manufactured using an aqueous solution polymerization process, it is also possible to carry out the polymerization process using multi-phase polymerization processing techniques such as inverse emulsion polymerization or inverse suspension polymerization procedures. See U.S. Pat. No. 4,340,706 (Obaysashi et al), issued Jul. 20, 1982, U.S. Pat. No. 4,506,052 (Flesher et al), issued Mar. 19, 1985, and U.S. Pat. No. 4,735,987 (Morita et al), issued Apr. 5, 1988, all of which are incorporated by reference, for processes involving inverse suspension polymerization. These absorbent polymers can synthesized or made in a variety of shapes and sizes, including fibers, granules, flakes or pulverulents. However, these absorbent polymers are most commonly supplied as absorbent particles or particulates.

One preferred class of hydrogel-forming absorbent polymers useful in the present invention are those which exhibit a high absorptive capacity. Absorptive capacity refers to the capacity of a given polymer material to absorb liquids with which it comes into contact. Absorptive capacity can vary significantly with the nature of the liquid being absorbed and with the manner in which the liquid contacts the polymer material. For purposes of this invention, Absorptive Capacity is defined in terms of the amount of Synthetic Urine absorbed by any given polymer material in terms of grams of Synthetic Urine per gram of polymer material in a procedure defined in the Test Methods section of U.S. Pat. No. 5,324,561 (Rezai et al), issued Jun. 23, 1994, which is incorporated by reference. Preferred absorbent polymers having a high absorptive capacity are those which have an Absorptive Capacity of at least about 20 grams, more preferably at least about 25 grams, of Synthetic Urine per gram of polymer material. Typically, these highly absorptive polymers have an Absorptive Capacity of from about 20 grams to about 70 grams of Synthetic Urine per gram of polymer material. Absorbent polymers having this relatively high absorptive capacity characteristic are especially useful in fluid storage components of the present invention since they hold desirably high amounts of discharged body exudates such as urine.

Another preferred class of hydrogel-forming absorbent polymers useful in the present invention are those having relatively high Saline Flow Conductivity (SFC) values and relatively high Performance Under Pressure (PUP) capacity. See copending U.S. application Ser. No. 219,574 (Goldman et al), filed Mar. 29, 1994, which is incorporated by reference, where SFC values and PUP capacity are defined and methods for measuring these parameters are provided. Absorbent polymers useful in the present invention can have SFC values of at least about $30 \times 10^{-7}$ $cm^3 sec/g$, preferably at least about $50 \times 10^{-7}$ $cm^3 sec/g$, and most preferably at least about $100 \times 10^{-7}$ $cm^3 sec/g$. Typically, these SFC values are in the range of from about 30 to about $1000 \times 10^{-7}$ $cm^3 sec/g$, more typically from about 50 to about $500 \times 10^{-7}$ $cm^3 sec/g$, and most typically from about 100 to about $350 \times 10^{-7}$ $cm^3 sec/g$. Absorbent polymers useful in the present invention generally have a PUP capacity at least about 23 g/g, preferably at least about 25 g/g, and most preferably at least about 29 g/g. Typically, these PUP capacity values are in the range of from about 23 to about 35 g/g, more typically from about 25 to about 33 g/g, and most typically from about 29 to about 33 g/g.

Surface crosslinking of the initially formed polymers is a preferred process for obtaining hydrogel-forming absorbent polymers having relatively high SFC and PUP capacity values. A number of processes for introducing surface crosslinks are disclosed in the art. These include those where: (i) a di- or poly-functional reagent(s) (e.g., glycerol, 1,3-dioxolan-2-one, polyvalent metal ions, polyquaternary amines) capable of reacting with existing functional groups within the hydrogel-forming absorbent polymer is applied to the surface of the hydrogel-forming absorbent polymer; (ii) a di- or poly-functional reagent that is capable of reacting with other added reagents and possibly existing functional groups within the hydrogel-forming absorbent polymer such as to increase the level of crosslinking at the surface is applied to the surface (e.g., the addition of monomer plus crosslinker and the initiation of a second polymerization reaction); (iii) no additional polyfunctional reagents are added, but additional reaction(s) is induced amongst existing components within the hydrogel-forming absorbent polymer either during or after the primary polymerization process such as to generate a higher level of crosslinking at or near the surface (e.g., heating to induce the formation of anhydride and or esters crosslinks between existing polymer carboxylic acid and/or hydroxyl groups and suspension polymerization processes wherein the crosslinker is inherently present at higher levels near the surface); and (iv) other materials are added to the surface such as to induce a higher level of crosslinking or otherwise reduce the surface deformability of the resultant hydrogel. Combinations of these surface crosslinking processes either concurrently or in sequence can also be employed. In addition to crosslinking reagents, other components can be added to the surface to aid/control the distribution of crosslinking (e.g., the spreading and penetration of the surface crosslinking reagents.) See copending U.S. application Ser. No. 219,574 (Goldman et al), filed Mar. 29, 1994, which is incorporated by reference.

Suitable general methods for carrying out surface crosslinking of hydrogel-forming absorbent polymers according to the present invention are disclosed in U.S. Pat. No. 4,541,871 (Obayashi), issued Sep. 17, 1985; published PCT application WO92/16565 (Stanley), published Oct. 1, 1992, published PCT application WO90/08789 (Tai), published Aug. 9, 1990; published PCT application WO93/05080 (Stanley), published Mar. 18, 1993; U.S. Pat. No. 4,824,901 (Alexander), issued Apr. 25, 1989; U.S. Pat. No. 4,789,861 (Johnson), issued Jan. 17, 1989; U.S. Pat. No. 4,587,308 (Makita), issued May 6, 1986; U.S. Pat. No. 4,734,478 (Tsubakimoto), issued Mar. 29, 1988; U.S. Pat. No. 5,164,459 (Kimura et. al.), issued Nov. 17, 1992; published German patent application 4,020,780 (Dahmen), published Aug. 29, 1991; and published European patent application 509,708 (Gartner), published Oct. 21, 1992; all of which are incorporated by reference. See also copending U.S. application Ser. No. 219,574 (Goldman et al), filed Mar. 29, 1994, which is incorporated by reference, and especially Examples 1 to 4.

While these hydrogel-forming absorbent polymers are preferably formed from the same monomers and have the same properties, this need not be the case. For example, some absorbent polymers can comprise a starch-acrylic acid graft copolymer while other absorbent polymers can comprise a slightly network crosslinked polymer of partially neutralized polyacrylic acid. Further, the absorbent polymers can vary in size, shape, absorptive capacity, or any other property or characteristic. In preferred embodiments of the present invention, the absorbent polymers consist essentially of slightly network crosslinked polymers of partially neutralized polyacrylic acid, each absorbent particle having similar properties.

One preferred fluid storage component according to the present invention having a relatively high concentration of these hydrogel-forming absorbent polymers is in the form of porous, absorbent macrostructures. These macrostructures are formed from a multiplicity of interconnected hydrogel-forming absorbent polymer particles. These macrostructures are capable of absorbing large quantities of aqueous body fluids (e.g., urine or menses) and then retaining such liquids under moderate pressures. Because they are formed from particles, these macrostructures have pores between adjacent particles. These pores are interconnected by intercommunicating channels such that the macrostructure is fluid permeable (i.e., has capillary transport channels).

Due to the bonds formed between the particles, the resultant aggregate macrostructures have improved structural integrity, increased fluid acquisition and distribution rates, and minimal gel-blocking characteristics. When wetted with aqueous fluids, the macrostructure swells generally isotropically even under moderate confining pressures, absorbs such fluids into the pores between the particles, and then imbibes such fluids into the particles. The isotropic swelling of the macrostructure allows the particles and the pores to maintain their relative geometry and spatial relationships even when swollen. Thus, the macrostructures are relatively "fluid stable" in that the particles do not dissociate from each other, thereby minimizing the incidence of gel blocking and allowing the capillary channels to be maintained and enlarged when swollen so that the macrostructure can acquire and transport subsequent loadings of liquid, even excess liquid. See U.S. Pat. No. 5,102,597 (Roe et al), issued Apr. 7, 1992, and U.S. Pat. No. 5,324,561 (Rezai et al), issued Jun. 23, 1994, which are incorporated by reference. As referred to herein, these macrostructures of interconnected particles are referred to as "fluid stable macrostuctures" or "fluid stable aggregates".

While these macrostructures can have a number of shapes and sizes, they are typically in the form of sheets, films, cylinders, blocks, spheres, fibers, filaments, or other shaped elements. These macrostructures will generally have a thickness or diameter between about 0.2 mm and about 10.0 mm. Preferably these macrostructures are in the form of sheets or strips. The terms "sheet" or "strips" as used herein describes macrostructures having a thickness of at least about 0.2 mm. The sheets or strips will preferably have a thickness between about 0.5 mm and about 10 mm, typically from about 1 mm to about 3 mm.

These macrostructures are formed by the joining or adhering together of adjacent particles. The adhesive agent is essentially the polymeric material that is present in the surface of these particles. When these particles are treated with a crosslinking agent and physically associated, the polymer material present in the surface of these particles is sufficiently plastic and cohesive (e.g., sticky) such that adjacent particles are adhered together, typically as discrete linking portions between the particles. The crosslinking reaction between the particles then sets this adhered structure.

In preparing these macrostructures, a crosslinking agent is used to provide crosslinking at the surface of the absorbent precursor particles. This typically occurs as a result of the crosslinking agent by reacting with the polymer material in these particles. Typically, the polymer material of the absorbent precursor particles has anionic, and preferably carboxy, functional groups that form a covalent, ester-type bond with the crosslinking agent. These portions of the absorbent particle that have been effectively crosslinked will swell less in the presence of aqueous (body) fluids relative to the other uncrosslinked portions of the particle.

Suitable crosslinking agents for this purpose can be nonionic and possess at least two functional groups per molecule capable of reacting with the carboxy group. See, for example, U.S. Pat. No. 5,102,597 (Roe et al), issued Apr. 7, 1992, which is incorporated by reference, and which discloses a variety of nonionic crosslinking agents. The particularly preferred nonionic crosslinking agent is glycerol. A preferred crosslinking agent for use in these macrostructures is an adduct of epichlorohydrin with certain types of monomeric or polymeric amines. See U.S. Pat. No. 5,324,561 (Rezai et al), issued Jun. 23, 1994, which is incorporated by reference and which discloses suitable cationic amino-epichlorohydrin adduct crosslinking agents. These amino-epichlorohydrin adducts, and especially the polymeric resin versions of these adducts, are preferred crosslinking agents because they react only with the polymer material at the surface precursor particles. In addition, the cationic functional groups (e.g., azetedinium groups) of these adducts, particularly polymeric resin versions, are believed to react very rapidly with the anionic, typically carboxy, functional groups of the polymer material of the absorbent particles, even at room temperature (e.g., at from about 18° to about 25° C.). Most preferred are certain polyamide-polyamine-epichlorohydrin resins particularly commercially marketed by Hercules Inc. under the trade name Kymeneg. Especially useful are Kymene® 557H, Kymene(® 557LX and Kymene® 557 Plus, which are the epichlorohydrin adducts of polyamide-polyamines that are the reaction products of diethylenetriamine and adipic acid. They are typically marketed in the form of aqueous solutions of the cationic resin material containing from about 10% to about 33% by weight of the resin active.

In preparing these porous, absorbent macrostructures, the absorbent particles are treated with the crosslinking agent, along with any other components or agents. For example, water is typically used with the crosslinking agent to form an aqueous treatment solution thereof. Water promotes the uniform dispersion of the crosslinking agent on the surface of the absorbent particles and causes permeation of the crosslinking agent into the surface regions of these particles. Water also promotes a stronger physical association between the treated precursor particles, providing greater integrity of the resultant interparticle bonded crosslinked aggregates. See U.S. Pat. No. 5,102,597 (Roe et al), issued Apr. 7, 1992 (nonionic crosslinking agents such as glycerol), and U.S. Pat. No. 5,324,561 (Rezai et al), issued Jun. 23, 1994 (cationic amino-epichlorohydrin adduct crosslinking agents), which are incorporated by reference.

It is particularly preferred that the treatment solution include a plasticizer, especially when cationic amino-epichlorohydrin adducts are used as the crosslinking agent. he preferred plasticizer is a mixture of glycerol and water, particularly when included as part of an aqueous treatment solution of the cationic amino-epichlorohydrin adduct, in a weight ratio of glycerol to water of from about 0.5:1 to about 2:1, preferably from about 0.8:1 to about 1.7:1. See U.S. Pat. No. 5,324,561 (Rezai et al), issued Jun. 23, 1994 which is incorporated by reference. Before, during, or after treatment with crosslinking agent, and optional plasticizer, the particles are physically associated together to form the aggregate macrostructures. A preferred method and apparatus for continuously forming these aggregate macrostructures into sheets is described in U.S. Pat. No. 5,324,561 (Rezai et al), issued Jun. 23, 1994 (cationic amino-epichlorohydrin adduct crosslinking agents), which are incorporated by reference. See especially FIG. 9 from this patent and its associated description.

Once the particles have been physically associated together to form an aggregate macrostructure, the crosslinking agent is reacted with the polymer material of the precursor particles, while maintaining the physical association of the particles, to provide effective surface crosslinking in the particles in the aggregate macrostructure. See U.S. Pat. No. 5,102,597 (Roe et al), issued Apr. 7, 1992 (nonionic crosslinking agents such as glycerol), and U.S. Pat. No. 5,324,561 (Rezai et al), issued Jun. 23, 1994 (cationic aminoepichlorohydrin adduct crosslinking agents), which are incorporated by reference. When amino-epichlorohydrin adducts are used as the crosslinking agent, this crosslinking reaction can occur at relatively low temperatures, including ambient room temperatures. Such ambient temperature curing is particularly desirable when the absorbent particles are treated a plasticizer, such as a mixture of water and glycerol. Curing at significantly above ambient temperatures can cause the plasticizer to be driven off due to its volatility, thus necessitating an additional step to plasticize the resulting aggregate macrostructure.

If desired, these macrostructures can include various types of fibers to act as reinforcing members. These include cellulose fibers, modified cellulose fibers, rayon, polypropylene, and polyester fibers such as polyethylene terephthalate (DACRON), hydrophilic nylon (HYDROFIL), and the like. Examples of other fiber materials are hydrophilized hydrophobic fibers, such as surfactant-treated or silica-treated thermoplastic fibers derived, for example, from polyolefins such as polyethylene or polypropylene, polyacrylics, polyamides, polystyrenes, polyurethanes and the like. In fact, hydrophilized hydrophobic fibers that are in and of themselves not very absorbent and which, therefore, do not provide webs of sufficient absorbent capacity to be useful in conventional absorbent structures, are suitable for use in these macrostructures by virtue of their good wicking properties. Synthetic fibers are generally preferred for use herein as the fiber component of the macrostructure. Most preferred are polyolefin fibers, preferably polyethylene fibers.

Other suitable fluid storage components according to the present invention can be in the form of a layer of hydrogel-forming absorbent polymer particles contained between two other fibrous layers, e.g., a laminated fluid storage component. Suitable laminated fluid storage components according to the present invention can be prepared using procedures similar to those described in U.S. Pat. No. 4,260,443 (Lindsay et al); U.S. Pat. No. 4,467,012 (Pedersen et al), issued Aug. 21, 1984; U.S. Pat. No. 4,715,918 (Lang), issued Dec. 29, 1987; U.S. Pat. No. 4,851,069 (Packard et al), issued Jul. 25, 1989; U.S. Pat. No. 4,950,264 (Osborn), issued Aug. 21, 1990; U.S. Pat. No. 4,994,037 (Bernardin), issued Feb. 19, 1991; U.S. Pat. No. 5,009,650 (Bernardin), issued Apr. 23, 1991; U.S. Pat. No. 5,009,653 (Osborn), issued Apr. 23, 1991; U.S. Pat. No. 5,128,082 (Makoui), Jul. 7, 1992; U.S. Pat. No. 5,149,335 (Kellenberger et al), issued Sep. 22, 1992; and U.S. Pat. No. 5,176,668 (Bernardin), issued Jan. 5, 1993 (all of which are incorporated by reference). These laminated fluid storage components can be in the form of thermally bonded fibrous layers, adhesively bonded fibrous layers (e.g., glue bonding between the fibrous layers or between the fibrous layers and the hydrogel-forming absorbent polymer particles), or fibrous layers that are held together by hydrogen bonding (e.g., by spraying the fibrous layers with water followed by compaction).

If desired, the above macrostructures or absorbent particles can be attached to a substrate to form the fluid storage components. The substrate can provide a variety of functions, including: (1) improving the distribution of fluids to be absorbed by the macrostructure/particles; and (2) supporting the macrostructure/particles by providing additional integrity, especially in the situation where the absorbent particles begin to swell after absorbing fluid. The substrate can be made from various materials known in the art such as cellulose fibers, nonwoven webs, tissue webs, foams, polyacrylate fibers, apertured polymeric webs, synthetic fibers, metallic foils, elastomers, and the like. Most such substrate materials can distribute fluids to, as well as support, the macrostructure/particles. Preferably, the substrate is comprised of cellulosic material or a material having cellulosic functionality. Preferred substrates for distributing fluids are cellulosic materials, fibrous webs, cellulosic fibrous webs, tissues, solid foams, cellulosic foams, and polyvinyl alcohol foams. Preferred substrates for supporting the macrostructure/particles are tissues, cellulosic materials, fibrous webs, nonwoven webs, fabrics, cellulosic fibrous webs, solid foams, cellulosic foams, and polyvinyl alcohol foams.

The substrate is preferably flexible and pliable to encourage such properties in the resulting absorbent composite with the macrostructure/particles. The substrate can be substantially resilient and non-stretchable, or it can be stretchable or deformable to a varying extent in response to forces exerted normal to and in the plane of the surface of the substrate. The thickness and basis weight (weight per unit area of substrate) of the substrate material can vary depending on the type of substrate and properties desired. The substrate can comprise a plurality of individual sheets, or plies, of a particular substrate material, or a combination of one or more substrate layers in a laminate. One such suitable substrate is a Bounty® sheet having a thickness of from about 0.02 mm to about 1.2 mm, more preferably from about 0.3 mm to about 0.8 mm; and a basis weight of from about 5 $g/m^2$ to about 100 $g/m^2$, more preferably from about 10 $g/m^2$ to about 60 $g/m^2$, and most preferably from about 15 $g/m^2$ to about 40 $g/m^2$. Another suitable substrate is a cellulose foam having a dry compressed thickness of from about 0.5 mm to about 3.0 mm, more preferably from about 0.8 mm to about 2.0 mm; a wet expanded thickness of from about 0.8 mm to about 6.0 mm, more preferably from about 1.0 mm to about 5.0 mm; and a basis weight of from about 50 $g/m^2$ to about 2,000 $g/m^2$, more preferably from about 100 $g/m^2$ to about 1,000 $g/m^2$.

Substrates suitable for supporting the macrostructure/particles typically have a dry tensile strength of from about 500 g/in to about 8,000 g/in, more preferably from about 1,000 g/in to about 3,000 g/in; a wet tensile strength of from about 200 g/in to about 5,000 g/in, though more preferably from about 400 g/in to about 1,000 g/in; and a wet burst strength of from about 100 g to about 2,000 g, though more preferably from about 200 g to about 1,000 g. Preferred substrates of this type include cellulosic fibrous webs such as paper towels and tissues such those disclosed in U.S. Pat. No. 3,953,638, issued Apr. 27, 1976, U.S. Pat. No. 4,469,735, issued Sept. 4, 1984, U.S. Pat. No. 4,468,428, issued Aug. 28, 1984, and U.S. Pat. No. 4,986,882, issued Jan. 22, 1991, all of which are incorporated by reference.

The porous absorbent macrostructure/particles can be attached to the substrate by a variety of chemical, physical, and adhesive agents. Adhesive agents for attaching the macrostructure/particles to substrate include glues and hot melt adhesives. Preferably, the bonding between the substrate and macrostructure/particles is achieved by depositing the precursor absorbent particles on the substrate, treating the deposited particles with the solution comprising a crosslinking agent and then curing the treated particles/ substrate as previously. In a preferred embodiment of this method, a cellulosic substrate (e.g., paper towel) is used. The precursor absorbent particles are then deposited on this cellulosic substrate. A treatment solution comprising an amino-epichlorohydrin adduct, preferably a polymeric epichlorohydrin-polyamide/polyamine wet strength resin such Kymene®, is then applied (e.g., sprayed) on the cellulosic substrate and the absorbent particles. The treated substrate/particles are then cured at ambient temperatures such that the particles are bonded to the cellulosic substrate.

To enhance the overall flexibility of the cores of the present invention, the fluid stable macrostructures may be slitted so as to be discontinuous. That is, the macrostructure strips may each be cut at various locations to form slits through the entire thickness (i.e., z-direction) of the structure. Such macrostructures are described in co-pending U.S. application Ser. No. 08/142,258 (filed Oct. 22, 1993 by Hsueh et al.), Ser. No. 08/550,181 (filed Oct. 30, 1995 by Rezai et al.), and Ser. No. 08/550,185 (filed Oct. 30, 1995 by Dierckes et al.), all of which are incorporated by reference herein. Upon stretching the slitted macrostructures in the y-direction, a "netted" material results. The open spaces between the hydrogel-containing continuous portion permits freer swelling of the hydrogel structure, and also increases permeability through this component.

The porous, absorbent macrostructures useful as fluid storage components according to the present invention can also be enclosed or enveloped within a tissue. Such tissue envelopes can keep loose absorbent particles from migrating within the absorbent core and can provide additional structural integrity to the macrostructure.

Regardless of the nature of the absorbent material utilized, it is important that the storage material be restrained from swelling to a significant degree into the fluid acquisition zone (i.e., in the x- and/or y-directions, particularly toward the interior of the absorbent core), while being free to swell in the z-direction. This will result in a larger acquisition zone to accept fluid gushes. As is discussed with regard to FIGS. 3 and 4, swelling into the fluid acquistion zone can be prevented by, for example, use of adhesive spot bonds. This may be particularly beneficial when discrete particles of absorbent polymer are used as the upper fluid storage material. In some instances, the arrangement of the various core materials will provide the desired restrained swelling.

b. Foam Materials

As indicated above, foam materials useful as the absorbent storage component of the present invention should, in addition to offering adequate fluid storage capacity, be capable of existing in a collapsed, or thin, state until contacted with a body fluid. The ability to remain in such as state is important in providing thin diapers that appeal to the consumer. The use of these foam materials provides the added advantage of swelling almost entirely in the z-direction. That is, upon imbibing fluid, the foams swell significantly in the z-direction, while essentially maintaining their length and width dimensions. This is important in that it allows for efficient formation of the fluid acquisition zone.

Representative foam materials that are useful in the present invention are those described in U.S. Pat. No. 5,387,207 ("'207 patent"), issued Feb. 7, 1995 to Dyer et al., which is incorporated herein by reference. Briefly, that patent describes polymeric foams derived from emulsions that have a relatively small amount of an oil phase (including the polymerizable monomers) and a relatively large amount of an aqueous phase. (Such emulsions are commonly referred to as high internal phase emulsions, or HIPEs.) These HIPE-derived foams are rendered hydrophilic by agents remaining after polymerization, or by post-polymerization treatment with a surfactant. The foams described in the '207 patent are open-celled. That is, the individual cells (also referred to as pores) that represent the space occupied by individual water droplets in the emulsion are interconnected by numerous small holes. These small holes in the walls of the cells allow fluid to transfer from one cell to another, throughout the entire foam structure.

The ability of the foams to remain in the "thin-until-wet" state is believed to be due to the capillary forces within the foam, particularly the foam's capillary pressure. To remain in the collapsed state until wetted, the capillary pressures within the foam must be equivalent or greater than the forces exerted by the elastic recovery or modulus of the foam polymer, which work to "spring" the foam back to its uncompressed thickness. Parameters that affect capillary pressure include capillary suction specific surface area, foam density, fluid surface tension and average cell size. Parameters that affect the modulus of the foams include monomer content comprising the polymer, as well as residual oil-soluble emulsifiers which tend to plasticize the polymer, thereby reducing polymer modulus. A complete list of preferred ranges for these parameters, as well as a discussion of other important properties of the foams, is set forth in the patent.

Co-pending U.S. application Ser. No. 08/563,866, which is incorporated by reference herein, was filed Nov. 29, 1995 by DesMarais et al., and also describes expandable foams that are useful in the present invention. Though these collapsable foams are also prepared from HIPEs, the preparation of emulsions with higher water-oil ratios provides even higher porosity, lower density structures. The foams are prepared from emulsions having a water phase to oil phase ratio of from about 55:1 to about 100:1. These foams have a specific surface area per foam volume of at least about 0.025 m$^2$/cc, preferably at least about 0.05 m$^2$/cc, more preferably at least about 0.07 m$^2$cc (the density being measured in the expanded state). The foams have a capillary suction specific surface area of at least about 3 m$^2$g, preferably from about 3 to about 15 m$^2$/g, more preferably from about 4 to about 13 m$^2$/g, and most preferably from about 5 to about 11 m$^2$/g. The foams have a foam density, as measured in the collapsed state, of from about 0.1 g/cc to about 0.2 g/cc, preferably from about 0.11 g/cc to about 0.15 g/cc, more preferably from about 0.12 g/cc to about 0.14 g/cc. The foams further exhibit a fluid surface tension of from about 15 to about 65 dynes/cm, preferably from about 20 to about 65 dynes/cm, more preferably from about 20 to about 65 dynes/cm. The average cell size of these foams is preferably less than about 50 µm, more preferably from about 5 µm to about 35 µm. These foams are particularly preferred as the fluid storage material when use of foams are desired. The foams will preferably exhibit a ratio of expanded (wet) to collapsed (dry) thickness of at least about 6:1, more preferably from about 6:1 to about 10:1; and a free absorbent capacity of from about 55 to about 100 ml of synthetic urine per gram of dry foam, more preferably from about 50 to 75 ml per gram.

3. Optional Lower Fluid Storage Component

Preferred absorbent core designs according to the present invention further comprise a lower fluid storage component. This lower fluid storage component is positioned underneath the lower fluid acquisition/distribution component. A portion of this lower storage component is also positioned underneath the fluid acquisition zone. This lower fluid storage component is in fluid communication with the lower fluid acquisition/distribution component so as to be able to receive the acquired body fluids. Materials useful as the upper fluid storage component will also be useful as the optional lower fluid storage component. However, it is not necessary that this component be capable of swelling in the z-direction upon imbibing fluid. Thus, the skilled artisan will recognize that any material capable of absorbing a significant amount of fluid can be utilized as this component.

The lower fluid storage component may comprise a fiber/hydrogel composite, or only a hydrogel material. In this case, the lower storage component will preferably have a concentration of hydrogel of from about 30% to 100%, more preferably from about 70% to 100%, by total weight of the lower storage component. The lower storage component may also comprise a hydrophilic polymeric foam, including those discussed above. Foams that remain thin until wetted are preferred, again because they allow the manufacture, transport and store display of very thin absorbent articles.

D. Fluid Acquisition Zone

The fluid acquisition zone, formed in-part by the swollen upper storage component(s), creates a void space beneath the upper and lower acquisition/distribution layers. Because of the void space created by the acquisition zone, the absorbent cores according to the present invention can more easily handle "gushes" of discharged body fluids. This is especially important as portions of the absorbent core become saturated from prior multiple discharges of such fluids.

As can be seen by referring to the drawings, the fluid acquisition zone has three dimensions. The width (y-direction) and length (x-direction) of the acquisition zone is generally defined as the void area created by the fluid storage component(s), with the "top" of the zone being the lower surface of the upper acquisition/distribution component, and the "bottom" of the zone being the upper surface of the lower acquisition/distribution material. (The skilled artisan will realize that while core components are described as being "beneath", "above", etc., such terms do not exclude embodiments where relatively thin materials (e.g., tissue paper) are located between such components.) Where two lateral storage components are spaced apart, the width of the acquisition zone is the gap between these components. The length in this case will be determined by the length of the storage components. The depth of the zone will be the height (z-direction) of the swollen storage components.

The fluid acquisition zone may be of irregular shape in the x-y directions, though generally rectangular is preferred. Further, while the volume of the acquisition zone required will vary according to various factors (e.g., the rate of absorbency of the storage material; the absorbency rate and capacity of the acquistion material; the size of the wearer; etc.), it is preferred that the acquisition zone have a volume, when the storage material is wetted, of at least about 30 cc, preferably at least about 50 cc, and more preferably at least about 75 cc. Of course, when in the dry state, the acquisition zone volume will be significantly smaller.

Those skilled in the art will recognize that measuring acquisition zone volumes will be imprecise, given the nature of the materials employed as the storage and acquisition/distribution components. As such, the preferred volume ranges listed are illustrative only, and are not intended to limit the scope of the invention.

E. Topsheets

Topsheets useful in absorbent articles of the present invention are compliant, soft feeling, and non-irritating to the wearer's skin. These topsheets are fluid pervious to permit body fluids to readily penetrate through its thickness. A suitable topsheet can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

Preferred topsheets for use in the present invention are selected from high loft nonwoven topsheets and aperture formed film topsheets. Apertured formed films are especially preferred for the topsheet because they are pervious to body fluids and yet non-absorbent and have a reduced tendency to allow fluids to pass back through and rewet the wearer's skin. Thus, the surface of the formed film that is in contact with the body remains dry, thereby reducing body soiling and creating a more comfortable feel for the wearer. Suitable formed films are described in U.S. Pat. No. 3,929,135 (Thompson), issued Dec. 30, 1975; U.S. Pat. No. 4,324,246 (Mullane, et al), issued Apr. 13, 1982; U.S. Pat. No. 4,342,314 (Radel, et al), issued Aug. 3, 1982; U.S. Pat. No. 4,463,045 (Ahr et al), issued Jul. 31, 1984; and U.S. Pat. No. 5,006,394 (Baird), issued Apr. 9, 1991. Each of these patents are incorporated herein by reference. Particularly preferred microapertured formed film topsheets are disclosed in U.S. Pat. No. 4,609,518 (Curro et al), issued Sep. 2, 1986 and U.S. Pat. No. 4,629,643 (Curro et al), issued Dec. 16, 1986, which are incorporated by reference. The preferred topsheet for use in catamenial products of the present invention is the formed film described in one or more of the above patents and marketed on sanitary napkins by The Procter & Gamble Company of Cincinnati, Ohio as "DRI-WEAVEO®."

The body surface of the formed film topsheet can be hydrophilic so as to help body fluids to transfer through the topsheet faster than if the body surface was not hydrophilic so as to diminish the likelihood that fluid will flow off the topsheet rather than flowing into and being absorbed by the absorbent structure. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated by reference. Alternatively, the body surface of the topsheet can be made hydrophilic by treating it with a surfactant such as is described in the above referenced U.S. Pat. No. 4,950,254, incorporated herein by reference.

F. Backsheets

Backsheets useful in absorbent articles of the present invention are typically impervious to body fluids and are preferably manufactured from a thin plastic film, although other flexible fluid impervious materials may also be used. As used herein, the term "flexible" refers to materials that are compliant and will readily conform to the general shape and contours of the human body. The backsheet prevents body fluids absorbed and contained in the absorbent core from wetting articles that contact the such as pants, pajamas, undergarments, and the like. The backsheet can comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheet can permit vapors to escape from the absorbent core (i.e., breathable) while still preventing body fluids from passing through the backsheet.

Particularly desirable backsheets can be made from a structural elastic-like film (SELF) web. A structural elastic-like film web is an extensible material that exhibits an elastic-like behavior in the direction of elongation without the use of added elastic materials. The SELF web includes a strainable network having at least two contiguous, distinct, and dissimilar regions. One of the regions is configured so that it will exhibit resistive forces in response to an applied axial elongation in a direction parallel to the predetermined axis before a substantial portion of the other region develops significant resistive forces to the applied elongation. At least one of the regions has a surface-path length that is greater than that of the other region as measured substantially parallel to the predetermined axis while the material is in an untensioned condition. The region exhibiting the longer surface-path length includes one or more deformations that extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-path length to enter the plane of applied elongation, whereupon the SELF web exhibits second resistive forces to further elongation. The total resistive forces to elongation are higher than the first resistive forces to elongation provided by the first region. SELF webs suitable for the present invention are more completely described in the copending, commonly assigned U.S. patent application Ser. No. 08/203,456 entitled "Absorbent Article with Multiple Zone Structural Elastic-Like Film Web Extensible Waist Feature" filed by Donald C. Roe, et al. on Feb. 24, 1994, which is incorporated herein by reference.

G. Absorbent Articles

The absorbent articles of the present invention generally comprise: (1) a topsheet; (2) a backsheet; and (3) an absorbent core of the present invention positioned between the topsheet and the backsheet. As used herein, the term "absorbent article" refers to articles that absorb and contain body fluids, and more specifically refers to articles that are placed against or in proximity to the body of the wearer to absorb and contain the various fluids discharged from the body. Additionally, "disposable" absorbent articles are those which are intended to be discarded after a single use (i.e., the original absorbent article in its whole is not intended to be laundered or otherwise restored or reused as an absorbent article, although certain materials or all of the absorbent article may be recycled, reused, or composted). A preferred embodiment of a disposable absorbent article according to the present invention is a diaper. As used herein, the term "diaper" refers to a garment generally worn by infants and incontinent persons that is worn about the lower torso of the wearer. It should be understood, however, that the present invention is also applicable to other absorbent articles such as incontinent briefs, incontinent pads, training pants, diaper inserts, catamenial pads, sanitary napkins, facial tissues, paper towels, and the like.

The absorbent core used in the absorbent articles of the present invention comprises at least one fluid storage component, as previously described, that is located relatively remote from the wearer. This is so the fluid that is temporarily located in the fluid acquistion zone is remote from the wearer, so as to avoid rewet and to enhance acquistions rates.

In a preferred embodiment, the absorbent core comprises at least and preferably two fluid storage components (in the form of strips) that are laterally spaced apart. By "laterally spaced apart" is meant that there is a gap between the fluid storage components. When these laterally spaced storage components swell in the z-direction upon absorbing body fluid, this gap between the fluid storage components, together with the acquisition/distribution layers positioned above and below, defines the fluid acquisition zone for receiving discharged body fluids. At least a portion of this fluid acquisition zone comprises a void space underneath the overlying upper acquisition/distribution component. Because of the void space in this acquisition zone, the absorbent core according to the present invention can more easily handle "gushes" of discharged body fluids. This is especially important as portions of the absorbent core become saturated from prior multiple discharges of such fluids.

Absorbent cores according to the present invention also comprise an upper fluid acquisition/distribution component that is capable of transporting the discharged body fluids to other components in the absorbent core. Given its location in the cores of the present invention, it is apparent that the primary function of this component is to rapidly acquire fluid gushes, and give those fluids up to other components so as to be free to accept the next fluid insult. As such, it is preferred that the upper acquisition/distribution component be constructed accordingly. To this end, it is preferred that this component contain little or no hydrogel-forming polymer. This upper fluid acquisition/distribution component is at least partially positioned underneath and typically proximate to the fluid discharge region of the core so as to be able to receive these discharged body fluids.

Preferred is where the upper acquisition/distribution material comprises chemically stiffened fibers, particularly where the fibers are thermally bonded. It is further preferred that the basis weight be in the range of from about 0.08 g/sq.in. to about 0.30 g/sq.in., more preferably from about 0.08 g/sq.in to about 0.15 g/sq.in.; and that the density be in the range of from about 0.05 g/cc to about 0.30 g/cc; more preferably from about 0.05 g/cc to about 0.15 g/cc.

The absorbent cores of the present invention further comprise a lower fluid acquisition/distribution component that is capable of transporting the discharged body fluids to other components in the absorbent core. This lower fluid acquisition/distribution component is at least partially positioned underneath the fluid discharge region of the core, and is positioned below the fluid storage component(s). This component can be either chemically stiffened fibers, cellulose fibers (also referred to as airfelt), or a fiber/absorbent hydrogel-forming composite. Preferred is where the lower acquisition/distribution material comprises chemically stiffened fibers or cellulose fibers, particularly where the fibers are thermally bonded. It is further preferred that the basis weight be in the range of from about 0.08 g/sq.in. to about 0.30 g/sq.in., more preferably from about 0.08 g/sq.in to about 0.15 g/sq.in.; and that the density be in the range of from about 0.05 g/cc to about 0.30 g/cc; more preferably from about 0.05 g/cc to about 0.15 g/cc.

Where the lower acquisition/distribution component comprises a fiber/absorbent hydrogel composite, the component will preferably have a concentration of hydrogel of from about 10% to 65%, more preferably from about 15% to 30%, by total weight of the lower acquisition/distribution component.

In an alternative embodiment, absorbent cores according to the present invention comprise more than two (2) strips of storage material as the upper fluid storage component, positioned between the upper and lower fluid acquisition/distribution components. Where more than two strips are used, each should be laterally spaced from the others to provide channels between each strip. In reference to the figures, use of more than two spaced-apart to fluid storage components would result in more than one fluid acquisition zone. In one embodiment, four (4) strips of storage material are used, and form three channels, or three distinct fluid acquisition zones.

In another embodiment, the absorbent core comprises a lower fluid storage component. Materials useful for the upper fluid storage component may also be useful in the lower fluid storage component. However, it is not necessary that this component be capable of swelling in the z-direction upon imbibing fluid. Thus, the skilled artisan will recognize that any material capable of absorbing a significant amount of fluid can be utilized as this lower component.

Figure 2:
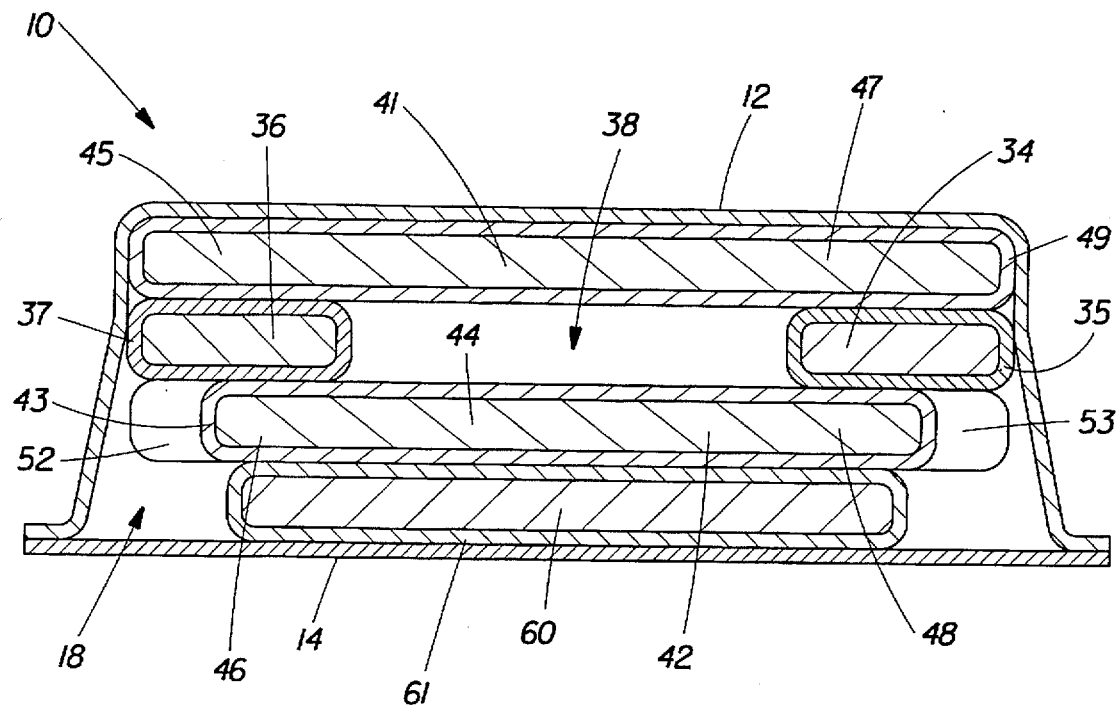
FIG. 2 is a cross-sectional view taken along line 2—2 of FIG. 1.

An embodiment of an absorbent article in the form of a diaper 10 having one such absorbent core according to the present invention is shown in FIG. 1. FIG. 1 is a top plan view of diaper 10 in a flat-out, uncontracted state (i.e., with any elastic-induced contraction removed) having a topsheet 12, a backsheet 14, and an absorbent core indicated generally as 18 that is positioned between topsheet 12 and backsheet 14. Topsheet 12 is shown as being transparent so as to better illustrate the various components of absorbent core 18. Also, the upper fluid acquisition/distribution layer 41 (which is depicted in FIG. 2) is not shown, to enable depiction of the other core components. However, in a preferred embodiment, this upper component is of approximately the same dimension as lower fluid acquisition/distribution layer 42, and is positioned between the topsheet 12 and two upper fluid storage components 34 and 36.

As also shown in FIG. 1, diaper 10 has a front waistband region 22, a back waistband region 24, a crotch region 26 and a periphery 28 that is defined by the outer edge of backsheet 14and which has longitudinal edges designated 30 and end edges designated as 32. The longitudinal axis of diaper 10 essentially runs parallel to longitudinal edges 30, while the transverse axis essentially runs parallel to end edges 32. The waistband regions 22 and 24 comprise those upper portions of the diaper 10, which when worn, encircle the waist of the wearer. The crotch region 26 is that portion of the diaper 10 between waistband regions 22 and 24, and comprises that portion of the diaper 10 which when worn, is positioned between the legs of the wearer and covers the lower torso of the wearer. Thus, the crotch region 26 defines the area of typical liquid deposition for a diaper 10 or other disposable absorbent article.

Topsheet 12 and backsheet 14 can be associated together in any suitable manner. As used herein, the term "associated" encompasses configurations where topsheet 12 is directly joined to backsheet 14 by affixing the topsheet directly to the backsheet, and configurations where the topsheet is indirectly joined to the backsheet by affixing the topsheet to intermediate members which in turn are affixed to the backsheet. Preferably, the topsheet 12 and backsheet 14 are affixed directly to each other by attachment means (not shown) such as an adhesive or any other attachment means as known in the art. For example, a uniform continuous layer of adhesive, a patterned layer of adhesive, or an array of separate lines or spots of adhesive may be used to affix topsheet 12 to backsheet 14. As shown in FIG. 1, topsheet 12 has a smaller size configuration than backsheet 14. However, topsheet 12 and backsheet 14 can both have the same, or a similar, size configuration (i.e., are coextensive) such they are joined together at periphery 28 of diaper 10. The size of the backsheet 14 is dictated by the size of the absorbent core 18 and the exact diaper design selected. In the embodiment shown in FIG. 1, the backsheet 14 has an hourglass-shaped configuration. However, other configuration such as rectangular, I-shaped and the like are also suitable.

Although not shown, diaper 10 can have elastic members that exert a contracting force on the diaper so that it configures more closely and more comfortably to the wearer. These elastic members can be assembled in a variety of well known configurations, such as those described generally in U.S. Pat. No. 3,860,003 (Buell), issued Jan. 14, 1975, which patent is incorporated by reference. The elastic members can be disposed adjacent the periphery 28 of the diaper 10, preferably along each longitudinal edge 30, so that the elastic members tend to draw and hold the diaper 10 against the legs of the wearer. Alternatively, the elastic members can be disposed adjacent either or both of the end edges 32 of diaper 10 to provide a waistband as well as or rather than leg cuffs. See, for example, U.S. Pat. No. 4,515,595 (Kievit et al), issued May 7, 1985, which is incorporated by reference. The elastic members are secured to the diaper 10 in an elastically contractible condition so that in a normally unrestrained configuration, these elastic members effectively contract or gather the diaper 10. The elastic members can be secured in an elastically contractible condition in at least two ways. For example, the elastic members can be stretched and secured while the diaper 10 is in an uncontracted condition. Alternatively, the diaper 10 can be contracted, for example, by pleating, and the elastic members secured and connected to the diaper 10 while they are in their unrelaxed or unstretched condition. The elastic members can extend essentially the entire length of the diaper 10 in the crotch region 26, or alternatively can extend the entire length of the diaper 10, or any other length suitable to provide an elastically contractible line. The length of these elastic members is typically dictated by the diaper's design.

Referring to FIG. 1 and especially FIG. 2, absorbent core 18 has an upper acquisition/distribution layer 41 located adjacent topsheet 12. The core 18 further comprises two upper fluid storage components 34 and 36 in the form of rectangular strips that comprise hydrogel-forming absorbent polymer (or a collapsable, hydrophilic polymeric foam) that are positioned between upper continuous acquisition/distribution layer 41 and lower continuous fluid acquisition/distribution component 42. The fluid storage components 34 and 36 are each respectively wrapped in a fluid pervious paper tissue 35 and 37, as shown specifically in FIG. 2. These wrapped fluid storage components 34 and 36 are laterally spaced apart and define the fluid acquisition zone identified generally as 38. This fluid acquisition zone 38 is generally in the fluid discharge region of diaper 10.

The upper continuous fluid acquisition/distribution component 41 is in the form of chemically stiffened fibers, and is optionally wrapped in tissue 49. Though acquistion/ distribution component 41 is shown in FIG. 2 as being wrapped by tissue 49, preferred is where this component is not tissue-wrapped. (Where this component contains absorbent hydrogel-forming polymer, it may be preferred to wrap the component with tissue.) This upper fluid acquisition/ distribution component 41 has lateral portion 45 and 47. Lateral portion 45 is positioned above and in fluid communication with fluid storage component 36, while lateral portion 47 is positioned above and in fluid communication with fluid storage component 34.

The lower continuous fluid acquisition/distribution component 42 is in the form a fibrous web that is also wrapped in a paper tissue 43. The middle portion 44 of this fluid acquisition/distribution component 42 is positioned underneath the fluid acquisition zone 38. This fluid acquisition/ distribution component 42 also has lateral portion 46 and 48. Lateral portion 46 is positioned underneath and in fluid communication with fluid storage component 36, while lateral portion 48 is positioned underneath and in fluid communication with fluid storage component 34. As shown in FIG. 1, fluid distribution component 42 has arcuate concave edges 52 and 53 in the crotch section 26 of diaper 10 and thus assumes a somewhat hourglass shape.

As shown particularly in FIG. 2, absorbent core 18 further includes a lower fluid storage component 60 in the form of a rectangular strip that comprises hydrogel-forming absorbent polymer or an absorbent foam material, and is wrapped in a paper tissue 61. This lower fluid storage component 60 has approximately the same length as fluid storage components 34 and 36, and is positioned underneath and in fluid communication with middle portion 44 of fluid distribution component 42. Lower storage component 60 is wider (in the y-direction) than the fluid acquisition zone 38 that is formed, in part, by the storage components 34 and 36. This lower fluid storage component 60 is positioned underneath the fluid acquisition zone 38.

As shown in FIG. 1, lower fluid distribution component 42 is somewhat longer in length than upper fluid storage components 34 and 36, as well as lower fluid storage component 60, which is positioned beneath lower acquisition/distribution component 42. (Lower storage component 60 is depicted as a broken line in FIG. 1.)

Upon first exposure to aqueous body fluids, upper storage components 34 and 36 begin to swell, increasing in caliper by at least 2 mm when fully saturated. This increase in caliper increases the void volume of the acquisition zone 38. Consequently, the absorbent article is better able to handle subsequent "gushes" of aqueous body fluids. Preferably, the upper storage components will expand by at least 100% in the z-direction. Of course, because the length and width of the fluid acquisition zone will also affect the core's void volume, 100% z-direction expansion may not be required in such cores.

Figure 3:
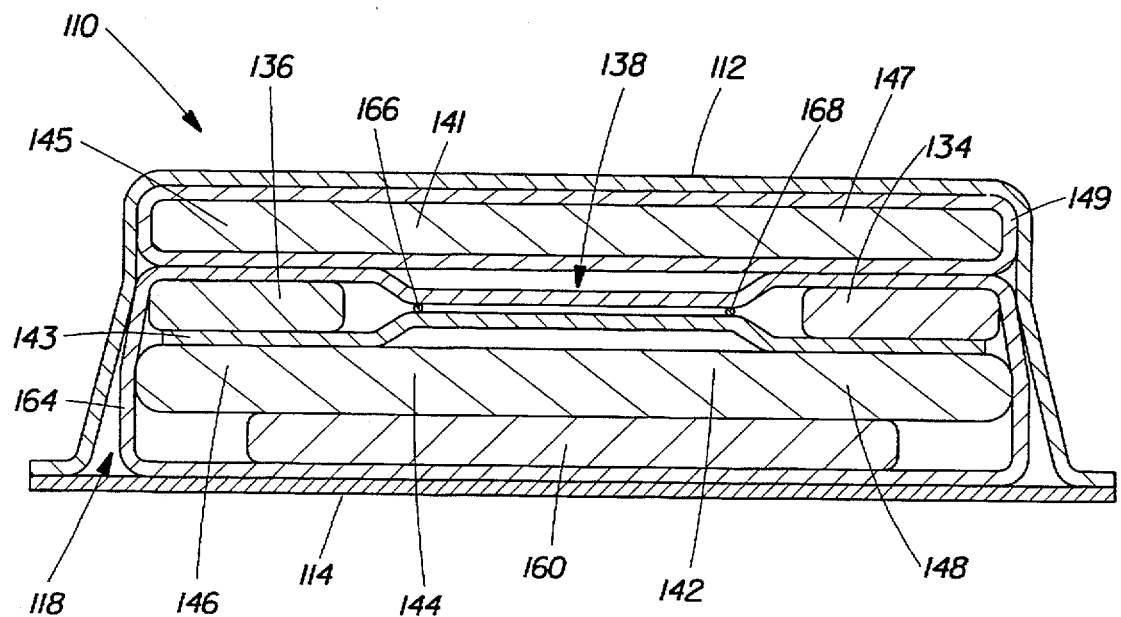
FIG. 3 is a cross-sectional view of an absorbent article showing an alternative absorbent core according to the present invention.

FIG. 3 shows a cross section of an absorbent article 110 having a topsheet 112, a backsheet 114 and an alternative absorbent core 118 positioned between the topsheet and the backsheet. Absorbent core 118 has an upper acquisition/ distribution layer 141 located adjacent topsheet 112. The core 118 further comprises two upper fluid storage components 134 and 136 in the form of rectangular strips that comprise hydrogel-forming absorbent polymer (or a collapsable, hydrophilic polymeric foam) that are positioned between upper continuous acquisition/distribution layer 141 and lower continuous fluid acquisition/distribution component 142. These fluid storage components 134 and 136 are laterally spaced apart and define the fluid acquisition zone identified generally as 138. This fluid acquisition zone 138 is generally in the fluid discharge region of diaper 110. A paper tissue layer 143 is positioned between these upper fluid storage components 134 and 136 and the lower fluid acquisition/distribution component 142.

The upper continuous fluid acquisition/distribution component 141 is in the form of a a web of chemically stiffened fibers, and is optionally wrapped in tissue 149. This upper fluid acquisition/distribution component 141 has lateral portion 145 and 147. Lateral portion 145 is positioned above and in fluid communication with fluid storage component 136, while lateral portion 147 is positioned above and in fluid communication with fluid storage component 134.

The lower continuous fluid acquisition/distribution component 142 is in the form a fibrous web. The middle portion 144 of this fluid acquisition/distribution component 142 is positioned underneath the fluid acquisition zone 138. This fluid acquisition/distribution component 142 also has lateral portion 146 and 148. Lateral portion 146 is positioned underneath and in fluid communication with fluid storage component 136, while lateral portion 148 is positioned underneath and in fluid communication with fluid storage component 134.

Absorbent core 118 further includes a lower fluid storage component 160 that comprises hydrogel-forming absorbent polymer or an absorbent polymeric foam. This lower fluid storage component 160 is positioned underneath and in fluid communication with middle portion 144 of fluid distribution component 142. This lower fluid storage component 160 is also positioned underneath the fluid acquisition zone 138, and is wider than the fluid acquistion zone 138. That is, the storage component 160 is wider than the gap between fluid storage components 134 and 136.

As shown in FIG. 3, the components of absorbent core 118, with the exception of the upper fluid acquisition/ distribution layer 141, are wrapped within a paper tissue 164. Tissue 164 is adhesively bonded to tissue 143 at the points indicated by 166 and 168.

Upon first exposure to aqueous body fluids, upper storage components 134 and 136 begin to swell, increasing in caliper by at least 2 mm when fully saturated. Adhesive bonds 166 and 168prevent lateral expansion of storage components 134 and 136 into acquisition zone 138. The increase in caliper increases the void volume of the acquisition zone 138. Consequently, the absorbent article is better able to handle subsequent "gushes" of aqueous body fluids.

Figure 4:
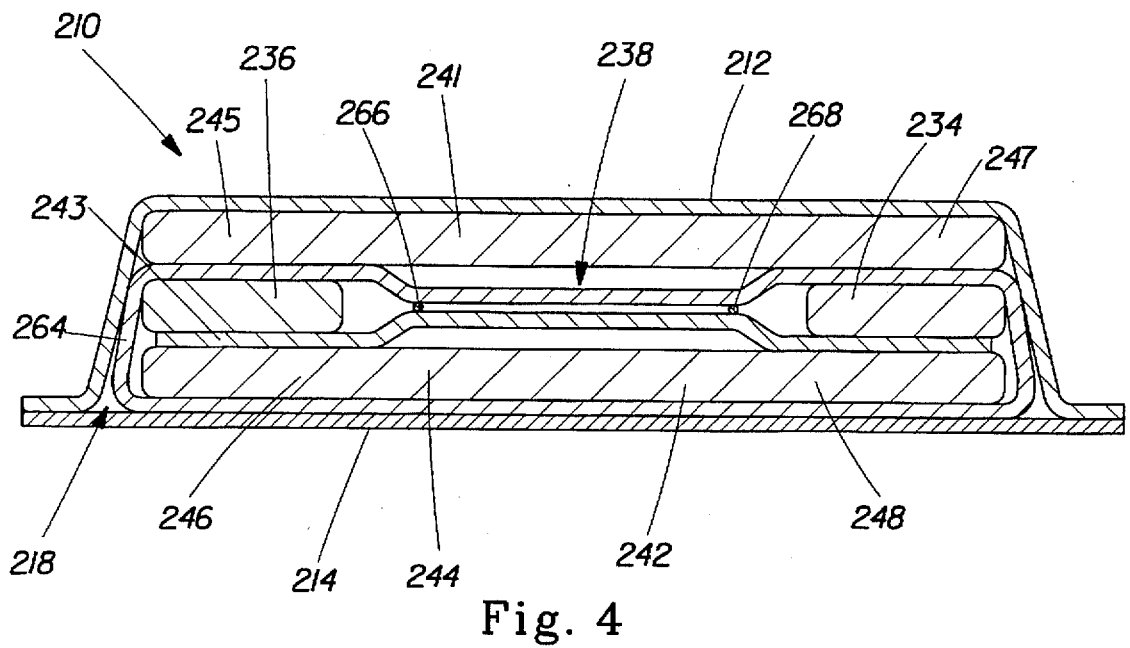
FIG. 4 is a cross-sectional view of an absorbent article showing another alternative absorbent core according to the present invention.

FIG. 4 shows a cross section of an absorbent article 210 having a topsheet 212, a backsheet 214 and another alternative absorbent core 218 positioned between the topsheet and the backsheet. This alternate absorbent core 218 has an upper acquisition/distribution layer 241 located adjacent topsheet 212. The core 218 further comprises two upper fluid storage components 234 and 236 in the form of rectangular strips that comprise hydrogelforming absorbent polymer (or a collapsable, hydrophilic polymeric foam) that are positioned between upper continuous acquisition/ distribution layer 241 and lower continuous fluid acquisition/distribution component 242. These fluid storage components 234 and 236 are laterally spaced apart and define the fluid acquisition zone identified generally as 238. This fluid acquisition zone 238 is generally in the fluid discharge region of diaper 210. A paper tissue layer 243 is positioned between these upper fluid storage components 234 and 236 and the lower fluid acquisition/distribution component 242.

The upper continuous fluid acquisition/distribution component 241 is in the form of a web of chemically stiffened cellulosic fibers. This upper fluid acquisition/distribution component 241 has lateral portion 245 and 247. Lateral portion 245 is positioned above and in fluid communication with fluid storage component 236, while lateral portion 247 is positioned above and in fluid communication with fluid storage component 234.

The lower continuous fluid acquisition/distribution component 242 is in the form a fibrous web. The middle portion 244 of this fluid acquisition/distribution component 242 is positioned underneath the fluid acquisition zone 238. This fluid acquisition/distribution component 242 also has lateral portion 246 and 248. Lateral portion 246 is positioned underneath and in fluid communication with fluid storage component 236, while lateral portion 248 is positioned underneath and in fluid communication with fluid storage component 234.

As shown in FIG. 4, the components of absorbent core 218, with the exception of upper fluid acquisition/ distribution layer 241, are wrapped within a paper tissue 264. Tissue 264 is adhesively bonded to tissue 243 at the points indicated by 266 and 268.

Upon first exposure to aqueous body fluids, upper storage components 234 and 236 begin to swell, increasing in caliper by at least 2 mm when fully saturated. Adhesive bonds 266 and 268 prevent lateral expansion of storage components 234 and 236 into acquisition zone 238. The increase in caliper increases the void volume of the acquisition zone 238. Consequently, the absorbent article is better able to handle subsequent "gushes" of aqueous body fluids.

Figure 5:
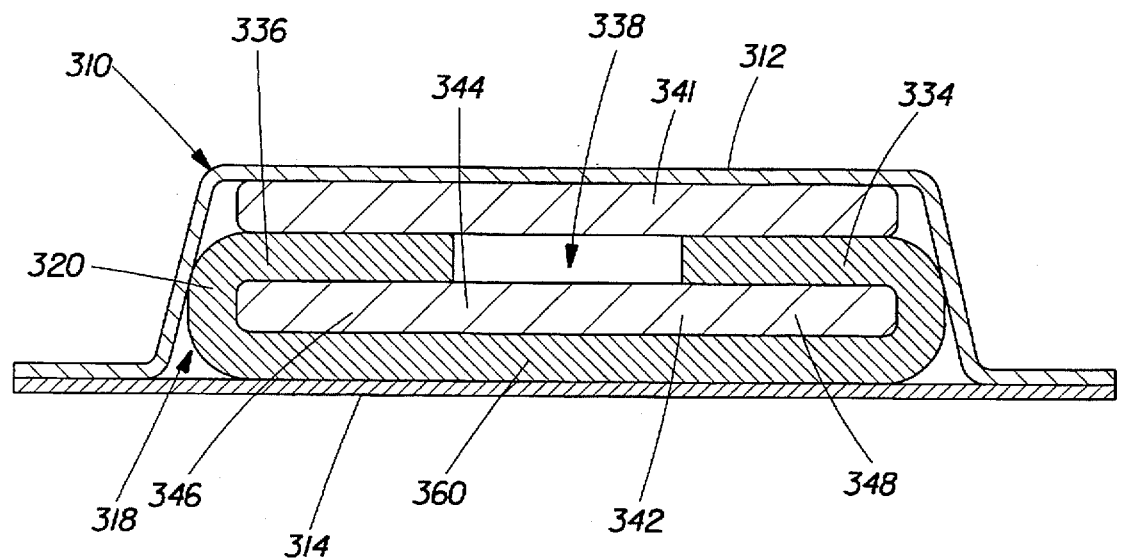
FIG. 5 is a cross-sectional view of an absorbent article showing another alternative absorbent core according to the present invention.

FIG. 5 shows a cross section of an absorbent article 310 having a topsheet 312, a backsheet 314 and yet another alternative absorbent core 318 positioned between the topsheet and the backsheet. This alternative absorbent has an upper fluid acquisition/ distribution layer 341 located adjacent topsheet 312. The core 318 further comprises a continuous component 320 comprising hydrogel-forming absorbent polymer or an absorbent polymeric foam that is partially wrapped around lower fluid distribution component 342, this continuous component 320 having the ability to expand in the z-direction upon absrobing body fluids. Continuous component 320 includes upper fluid storage components or sections 334 and 336 that are positioned between upper fluid acqustion/distribution layer 341 and lower fluid distribution component 342; and a lower fluid storage component or section 360 that is underneath lower fluid distribution component 342. The gap between fluid storage components/sections 334 and 336 define the fluid acquisition zone identified generally as 338. Middle portion 341 of fluid lower distribution component 342 is underneath fluid acquisition zone 338. Lateral portion 346 of lower fluid distribution component 342 is positioned underneath and in fluid communication with fluid storage component 336, while lateral portion 348 is positioned underneath and in fluid communication with fluid storage component 334. Lower fluid storage component or section 360 is underneath and in fluid communication with fluid distribution component 342.

Upon first exposure to aqueous body fluids, upper storage components or sections 334 and 336 begin to swell, increasing in caliper by at least 2 mm when fully saturated.

The increase in caliper increases the void volume of the acquisition zone 338. Consequently, the absorbent article is better able to handle subsequent "gushes" of aqueous body fluids.

Figure 6:
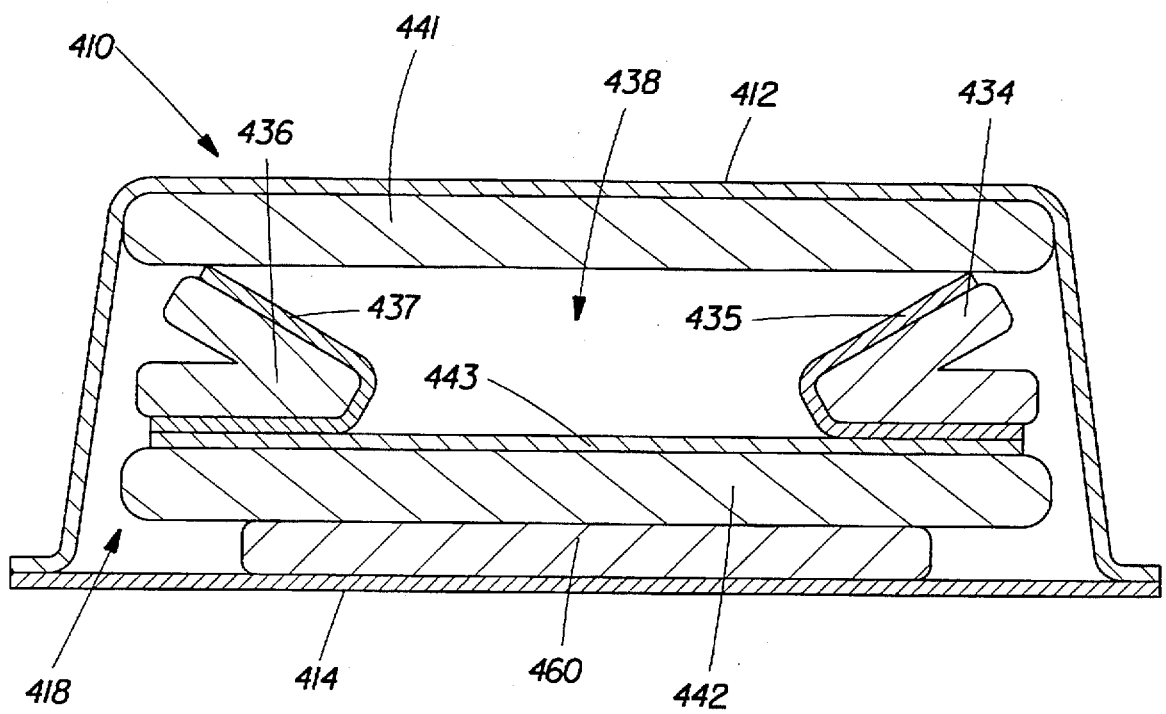
FIG. 6 is a cross-sectional view of an absorbent article showing yet another alternative absorbent core according to the present invention.

FIG. 6 shows a cross section of an absorbent article 410 having a topsheet 412, a backsheet 414 and an alternative absorbent core 418 positioned between the topsheet and the backsheet. This alternative absorbent core 418 also has to two upper fluid storage components 434 and 436 that comprise hydrogel-forming absorbent polymer or a polymeric absorbent foam, positioned between upper fluid acquisition/distribution layer 441 and lower fluid acquisition/distribution layer 442. These fluid storage components 434 and 436 are laterally spaced apart and define the fluid acquisition zone identified generally as 438. These fluid storage components 434 and 436 are further bonded to substrates 435and 437 (when they comprise hydrogel-forming absorbent polymer) and are folded in a c-shape as shown in FIG. 6.

A paper tissue layer 443 is positioned under the upper fluid storage components 434 and 436 and over lower fluid distribution component 442. This lower fluid distribution component 442 is positioned underneath and in fluid communication with fluid storage components 434 and 436 and under fluid acquisition zone 438.

Absorbent core 418 further includes a lower fluid storage component 460 that comprises hydrogel-forming absorbent polymer. This lower fluid storage component 460 is positioned underneath and in fluid communication with lower fluid distribution component 442. This lower fluid storage component 460 is also positioned underneath the fluid acquisition zone 438.

Upon first exposure to aqueous body fluids, upper storage components 434 and 436 begin to swell, increasing in caliper by at least 2 mm when fully saturated. Substrate layers 435 and 437 prevent lateral expansion of storage components 434 and 436 into acquisition zone 438. The increase in caliper increases the void volume of the acquisition zone 438. Consequently, the absorbent article is better able to handle subsequent "gushes" of aqueous body fluids.

What is claimed is:

1. An absorbent core capable of absorbing discharged aqueous body fluids, the absorbent core comprising:

(1) an upper fluid acquisition/distribution component capable of receiving aqueous fluids, the upper fluid acquisition/distribution component being positioned in the fluid discharge region of the absorbent core;

(2) at least one upper fluid storage component positioned at least partially underneath and in fluid communication with the upper fluid acquisition/distribution component, said at least one fluid storage component being capable of expanding in the z-direction by at least 100% when fully saturated with aqueous body fluids to form a fluid acquisition zone and being restrained from substantial swelling toward the interior of said fluid acquisition zone formed from said expansion of said at least one fluid storage component;

(3) a fluid acquisition zone capable of receiving aqueous body fluids, the fluid acqustion zone being at least partially surrounded by said at least one upper fluid storage component and positioned at least partially beneath the fluid discharge region of the absorbent core; and (4) a lower fluid acquisition/distribution component capable of acquiring and transporting aqueous body fluids, the lower fluid acquisition/distribution component being positioned at least partially underneath and in fluid communication with said at least one upper fluid storage component.

2. The absorbent core of claim 1 further comprising (5) at least one lower fluid storage component positioned underneath the lower fluid acquisition/distribution component and in fluid communication therewith, at least a portion of this lower storage component being positioned underneath the fluid acquisition zone.

3. The absorbent core of claim 2 wherein the lower fluid storage component comprises from about 70 to 100%, by weight of the storage component, of hydrogel-forming absorbent polymer.

4. The absorbent core of claim 3 wherein the hydrogel-forming absorbent polymer has an Absorptive Capacity of at least about 25 grams of Synthetic Urine per gram of polymer material; a Saline Flow Conductivity value of at least about $30 \times 10^{-7}$ cm$^3$sec/g; and a Performance Under Pressure capacity value of at least about 23 g/g.

5. The absorbent core of claim 2 wherein the lower fluid storage component(s) comprises a fluid stable macrostructure comprising interconnected, hydrogel-forming absorbent polymer particles.

6. The absorbent core of claim 5 wherein the fluid stable macrostructure further comprises a substrate to which the interconnected, hydrogel-forming absorbent polymer particles are bonded.

7. An absorbent article for absorbing discharged aqueous body fluids, the absorbent article comprising:
   (A) a topsheet;
   (B) a backsheet; and
   (C) the absorbent core of claim 6 located between the topsheet and backsheet.

8. An absorbent article for absorbing discharged aqueous body fluids, the absorbent article comprising:
   (A) a topsheet;
   (B) a backsheet; and
   (C) the absorbent core of claim 2 located between the topsheet and backsheet.

9. The absorbent core of claim 1 wherein the core comprises two upper fluid storage components.

10. The absorbent core of claim 9 wherein the two upper fluid storage components are strips that run longitudinally in the absorbent core, wherein the components are laterally spaced apart so as to form the fluid acquistion zone upon contact with aqueous body fluids.

11. The absorbent core of claim 10 further comprising at least one lower fluid storage component positioned underneath the lower fluid acquisition/distribution component and being wider than the fluid acquisition zone formed by the laterally spaced apart upper fluid storage components.

12. An absorbent article for absorbing discharged aqueous body fluids, the absorbent article comprising:
   (A) a topsheet;
   (B) a backsheet; and
   (C) the absorbent core of claim 11 located between the topsheet and backsheet.

13. The absorbent core of claim 10 wherein both laterally spaced apart upper fluid storage components comprise: a) a fluid stable macrostructure comprising interconnected, hydrogel-forming absorbent polymer particles; and b) a substrate to which the interconnected, hydrogel-forming absorbent polymer particles are bonded.

14. The absorbent core of claim 13 wherein each of the laterally spaced apart upper fluid storage components is c-folded longitudinally to form a two layer component.

15. The absorbent core of claim 10 wherein a) a first tissue paper is positioned below the two upper fluid storage components and above the lower fluid acquisition/distribution; b) the two upper fluid storage components and the lower acquisition/distribution component are wrapped by a second tissue paper; and c) the first and second tissue papers are bonded at a location between the upper storage components so as to prevent swelling of the storage components into the fluid acquisition zone.

16. The absorbent core of claim 10 wherein the two upper fluid storage components are separately wrapped by tissue paper, and wherein the upper fluid acquisition/distribution component and the lower fluid/acquisition component are each optionally wrapped by a separate tissue paper.

17. An absorbent article for absorbing discharged aqueous body fluids, the absorbent article comprising:
   (A) a topsheet;
   (B) a backsheet; and
   (C) the absorbent core of claim 16 located between the topsheet and backsheet.

18. The absorbent core of claim 1 wherein the upper fluid storage component(s) comprises from about 50 to 100%, by weight of the respective storage component, of hydrogel-forming absorbent polymer.

19. The absorbent core of claim 18 wherein the upper fluid storage component(s) comprises from about 70 to 100%, by weight of the respective storage component, of hydrogel-forming absorbent polymer.

20. The absorbent core of claim 18 wherein the hydrogel-forming absorbent polymer has an Absorptive Capacity of at least about 25 grams of Synthetic Urine per gram of polymer material.

21. The absorbent core of claim 18 wherein the hydrogel-forming absorbent polymer has a Saline Flow Conductivity value of at least about $30 \times 10^{-7}$ cm$^3$sec/g and a Performance Under Pressure capacity value of at least about 23 g/g.

22. An absorbent article for absorbing discharged aqueous body fluids, the absorbent article comprising:
   (A) a topsheet;
   (B) a backsheet; and
   (C) the absorbent core of claim 18 located between the topsheet and backsheet.

23. The absorbent core of claim 1 wherein the upper fluid storage component(s) comprises a fluid stable macrostructure of interconnected, hydrogel-forming absorbent polymer particles.

24. The absorbent core of claim 23 wherein the fluid stable macrostructure further comprises a substrate to which the interconnected, hydrogel-forming absorbent polymer particles are bonded.

25. The absorbent core of claim 24 wherein the fluid stable macrostructure is slitted through its entire thickness so as to be discontinuous.

26. The absorbent core of claim 1 wherein the upper fluid storage component(s) comprises a collapsable polymeric foam material derived from a high internal phase water in oil emulsion.

27. The absorbent core of claim 26 wherein the polymeric foam material has:
   A) a specific surface area per foam volume of at least about 0.025 m$^2$/cc;
   B) a capillary suction specific surface area of at least about 3 m$^2$g;
   C) a foam density, as measured in the collapsed state, of from about 0.1 g/cc to about 0.2 g/cc;
   D) an average cell size of less than about 50 µm;
   E) a ratio of expanded to collapsed thickness of at least about 6:1; and
   F) a free absorbent capacity of from about 55 to about 100 ml of synthetic urine, per gram of foam.

28. An absorbent article for absorbing discharged aqueous body fluids, the absorbent article comprising:
   (A) a topsheet;
   (B) a backsheet; and (C) the absorbent core of claim 27 located between the topsheet and backsheet.

29. The absorbent core of claim 1 wherein the upper fluid acquisition/distribution layer comprises chemically stiffened cellulosic fibers.

30. The absorbent core of claim 29 wherein the upper fluid acquisition/distribution layer comprises chemically stiffened cellulosic fibers that are thermally bonded with a thermoplastic material.

31. The absorbent core of claim 30 wherein the upper fluid acquisition/distribution layer comprises essentially no hydrogel-forming absorbent polymer.

32. The absorbent core of claim 1 wherein the lower fluid acquisition/distribution layer comprises comprises from about 10 to about 30%, by weight of the lower fluid acquisition/distribution component, hydrogel-forming absorbent polymer.

33. An absorbent article for absorbing discharged aqueous body fluids, the absorbent article comprising:
  (A) a topsheet;
  (B) a backsheet; and
  (C) the absorbent core of claim 1 located between the topsheet and backsheet.

34. An absorbent core capable of absorbing discharged aqueous body fluids, said absorbent core comprising:
  (1) an upper fluid acquisition/distribution component capable of receiving aqueous fluids, the upper fluid acquisition/distribution component being positioned in the fluid discharge region of the absorbent core and comprising chemically stiffened cellulosic fibers that are thermally bonded with a thermoplastic material;
  (2) two upper fluid storage components capable of expanding in the z-direction by at least 100% when fully saturated with aqueous body fluids, the two upper fluid storage components being in the form of strips that run longitudinally in the absorbent core and are spaced apart so as to form a fluid acquisition zone upon contact with aqueous body fluids, and wherein both fluid storage components comprise a fluid stable macrostructure of interconnected, hydrogel-forming absorbent polymer particles;
  (3) a fluid acquisition zone capable of receiving aqueous body fluids, said fluid acquisition zone being at least partially surrounded by the two upper fluid storage components and positioned at least partially beneath the fluid discharge region of the absorbent core;
  (4) a lower fluid acquisition/distribution component capable of acquiring and transporting aqueous body fluids, the lower fluid acquisition/distribution component being positioned at least partially underneath and in fluid communication with said upper fluid storage components, wherein the lower fluid acquisition/distribution component comprises from 10 to about 30%, by weight, of a hydrogel-forming polymer; and
  (5) a lower fluid storage component positioned underneath the lower fluid acquisition/distribution component and in fluid communication therewith, the lower fluid storage component being wider than the fluid acquisition zone, wherein the lower fluid storage component comprises a fluid stable macrostructure of interconnected, hydrogel-forming absorbent polymer particles.

35. An absorbent article for absorbing discharged aqueous body fluids, the absorbent article comprising:
  (A) a topsheet;
  (B) a backsheet; and
  (C) the absorbent core of claim 34 located between the topsheet and backsheet.

36. A diaper comprising:
  (A) a topsheet;
  (B) a backsheet; and
  (C) an absorbent core located between the topsheet and backsheet, the absorbent core comprising:
    (1) an upper fluid acquisition/distribution component capable of receiving aqueous fluids, the upper fluid acquisition/distribution component being positioned in the fluid discharge region of the absorbent core;
    (2) at least one upper fluid storage component positioned at least partially underneath and in fluid communication with the upper fluid acquisition/distribution component, said at least one upper fluid storage component being capable of expanding in the z-direction by at least 100% when fully saturated with aqueous body fluids to form a fluid acquisition zone and being restrained from substantial swelling toward the interior of said fluid acquisition zone formed from said expansion of said at least one upper fluid storage component;
    (3) a fluid acquisition zone capable of receiving aqueous body fluids, said fluid acquistion zone being at least partially surrounded by said at least one upper fluid storage component and positioned at least partially beneath the fluid discharge region of the absorbent core; and
    (4) a lower fluid acquisition/distribution component capable of acquiring and transporting aqueous body fluids, the lower fluid acquisition/distribution component being positioned at least partially underneath and in fluid communication with said upper fluid storage component.

37. The diaper of claim 36 wherein the absorbent core further comprises:
  (5) at least one lower fluid storage component positioned underneath the lower fluid acquisition/distribution component and in fluid communication therewith, at least a portion of this lower storage component being positioned underneath the fluid acquisition zone.

38. The diaper of claim 36 wherein the absorbent core further comprises: a) a first tissue paper positioned below the two upper fluid storage components and above the lower fluid acquisition/distribution component is located; b) the two upper fluid storage components and the lower acquisition/distribution component wrapped by a second tissue paper; and c) the first and second tissue papers bonded at a location between the upper storage components so as to prevent swelling of the storage components into the fluid acquisition zone.

* * * * *